(12) United States Patent
Mekalanos

(10) Patent No.: US 9,533,032 B2
(45) Date of Patent: Jan. 3, 2017

(54) PROTEIN MATRIX VACCINES AND RELATED METHODS OF MAKING AND ADMINISTERING SUCH VACCINES

(71) Applicant: President and Fellows of Harvard College, Cambridge, MA (US)

(72) Inventor: John J. Mekalanos, Charlestown, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/950,113

(22) Filed: Nov. 24, 2015

(65) Prior Publication Data

US 2016/0136257 A1 May 19, 2016

Related U.S. Application Data

(62) Division of application No. 14/142,221, filed on Dec. 27, 2013, now Pat. No. 9,216,223, which is a division of application No. 11/890,565, filed on Aug. 7, 2007, now Pat. No. 8,642,042.

(60) Provisional application No. 60/933,764, filed on Jun. 8, 2007, provisional application No. 60/835,944, filed on Aug. 7, 2006.

(51) Int. Cl.
| | |
|---|---|
| A61K 39/00 | (2006.01) |
| A61K 39/095 | (2006.01) |
| A61K 39/385 | (2006.01) |
| A61K 39/07 | (2006.01) |
| A61K 47/42 | (2006.01) |
| A61K 39/02 | (2006.01) |
| A61K 39/112 | (2006.01) |
| A61K 39/09 | (2006.01) |

(52) U.S. Cl.
CPC ............. *A61K 39/095* (2013.01); *A61K 39/02* (2013.01); *A61K 39/0275* (2013.01); *A61K 39/0283* (2013.01); *A61K 39/07* (2013.01); *A61K 39/092* (2013.01); *A61K 39/385* (2013.01); *A61K 47/42* (2013.01); *A61K 2039/6037* (2013.01); *A61K 2039/645* (2013.01)

(58) Field of Classification Search
CPC .................................................. A61K 39/095
See application file for complete search history.

(56) References Cited

U.S. PATENT DOCUMENTS

| 4,707,543 A | 11/1987 | Zollinger et al. |
| 4,761,470 A | 8/1988 | Emini et al. |
| 5,153,312 A | 10/1992 | Porro |
| 5,565,204 A | 10/1996 | Kuo et al. |
| 5,961,970 A | 10/1999 | Lowell et al. |
| 6,476,201 B1 | 11/2002 | Lowell et al. |
| 6,821,331 B2 | 11/2004 | Damodaran |
| 8,642,042 B2 | 2/2014 | Mekalanos |
| 2008/0286297 A1 | 11/2008 | Florack et al. |
| 2014/0186399 A1 | 7/2014 | Mekalanos |

FOREIGN PATENT DOCUMENTS

WO    WO 95/33481    12/1995

OTHER PUBLICATIONS

Ada et al., "Carbohydrate-Protein Conjugate Vaccines," *Clin. Microbiol. Infect.* 9:79-85, 2003.
Akagi et al., "Preparation and Characterization of Biodegradable Nanoparticles Based on Poly(γ-Glutamic Acid) with L-Phenylalanine as a Protein Carrier," *J. Control. Release* 108:226-236, 2005.
Ascenzi et al., "Allosteric modulation of drug binding to human serum albumin," Mini Rev. Med. Chem. 6:483-489, 2006 (abstract only).
Aulinger et al., "Combining Anthrax Vaccine and Therapy: a Dominant-Negative Inhibitor of Anthrax Toxin is Also a Potent and Safe Immunogen for Vaccines," *Infect. Immun.* 73(6):3408-3414 (2005).
Bergquist et al., "Antibody Responses in Serum and Lung to Intranasal Immunization with *Haemophilus influenzae* Type b Polysaccharide Conjugated to Cholera Toxin B Subunit and Tetanus Toxoid," *APMIS* 106:800-806, 1998.
Buzzi et al., "CRM197 (Nontoxic Diphtheria Toxin): Effects on Advanced Cancer Patients," *Cancer Immunol. Immunother.* 53:1041-1048, 2004. (Abstract Only).
Cameron et al., "Essential Role for Verotoxin in Sustained Stress-Activated Protein Kinase and Nuclear Factor Kappa B Signaling, Stimulated by *Escherichia coli* O157:H7 in Vero cells," *Infect. Immun.* 70:5370-5380, 2002.
Carter, "Chapter 117: Conjugation of Peptides to Carrier Proteins via Glutaraldehyde," in: *The Protein Protocols Handbook* (ed. J.M. Walker) pp. 679-687 (Humana Press Inc., Totowa, NJ, 1996).
Chabot et al., "Anthrax Capsule Vaccine Protects Against Experimental Infection," *Vaccine* 23:43-47, 2004.
Cho et al., "Novel Mucosal Immunization with Polysaccharide-Protein Conjugates Entrapped in Alginate Microspheres," *J. Control. Release* 53:215-224, 1998.
Collins et al., "Analysis of the PiIQ secretin from *Neisseria meningitides* by transmission electron microscopy reveals a dodecameric quaternary structure," J. Bacteriol. 183:3825-3832, 2001.
Conlan et al., "Mice Vaccinated with the O-antigen of *Francisella tularensis* LVS Lipopolysaccharide Conjugated to Bovine Serum Albumin Develop Varying Degress of Protective Immunity Against Systemic or Aerosol Challenge with Virulent Type A and Type B Strains of the Pathogen," *Vaccine* 20(29-30):3465-3471 (2002).
Dick and Beurret, "Glycoconjugates of Bacterial Carbohydrate Antigens. A Survey and Consideration of Design and Preparation Factors," *Contrib. Microbiol. Immunol.* In: Conjugate Vaccines, Cruise et al. (Eds.) 10:48-114 (1989).
Figueiredo et al., "Characterization of Recombinant Tetanus Toxin Derivatives Suitable for Vaiccne Development," *Infect. Immun.* 63:3218-3221, 1995.

(Continued)

*Primary Examiner* — Albert Navarro
(74) *Attorney, Agent, or Firm* — Clark & Elbing LLP; Kristina Bieker-Brady

(57) ABSTRACT

The invention relates to vaccine compositions having a carrier protein and an antigen of interest entrapped in a complex, methods of making such vaccines, and methods of vaccine administration.

15 Claims, 16 Drawing Sheets

(56) References Cited

OTHER PUBLICATIONS

Giavedoni, "Developing Novel Conjugate HIV-1 Subunit Therapeutic Vaccines," Report Prepared for Commander, U.S. Army Medical Research and Material Command, Fort Detrick, Frederick, MD, Defence Technical Information Center (DTIC), Grant No. DAMD17-95-1-5029, pp. 1-14, Jun. 1997.
Granoff et al., "Effect of Immunity to the Carrier Protein on Antibody Responses to *Haemophilus influenzae* Type b Conjugate Vaccines," *Vaccine* 11 (Suppl. 1):S46-S51, 1993.
Hamšíková et al., "Immunogenicity of a Synthetic Peptide Corresponding to a Portion of the Heavy Chain of H3N2 Influenza Virus Haemagglutinin," *J. Gen. Virol.* 68:2249-2252, 1987.
Jakobsen et al., "Intranasal immunization with pneumococcal polysaccharide conjugate vaccines with nontoxic mutants of *Escherichia coli* heat-labile enterotoxins as adjuvants protects mice against invasive pneumococcal infections," *Infect. Immun.* 67: 5892-5897 (1999).
Kamboj et al., "Significant variation in the serotype-specific immunogenicity of the seven-valent *Streptococcus pneumoniae* capsular polysaccharide-$CRM_{197}$ conjugate vaccine occurs despite vigorous T cell help induced by the carrier protein," *Journal of Infectious Diseases* 187: 1629-1638 (2003).
Kersten and Crommelin, "Liposomes and ISCOMs," *Vaccine* 21: 915-920, 2003.
Latz et al., "*Haemophilus influenzae* Type b-Outer Membrane Protein Complex Glycoconjugate Vaccine Induces Cytokine Production by Engaging Human Toll-Like Receptor 2 (TLR2) and Requires the Presence of TLR2 for Optimal Immunogenicity," *J. Immunol.* 172(4):2431-2438 (2004).
Li et al., "Recombinant Forms of Tetanus Toxin Engineered for Examining and Exploiting Neuronal Trafficking Pathways," *J. Biol. Chem.* 276:31394-31401, 2001.
Lin et al., "Preparation of surface-modified albumin nanospheres," Biomaterials 18:559-565, 1997.
Lukač et al., "Toxoid of *Pseudomonas aeruginosa* Exotoxin A Generated by Deletion of an Active-Site Residue," *Infect. Immun.* 56:3095-3098, 1988.
Melton-Celsa et al., "Activation of Shiga Toxin Type 2d (Stx2d) by Elastase Involves Cleavage of the C-terminal Two Amino Acids of the $A_2$ Peptide in the Context of the Appropriate B Pentamer," *Mol. Microbiol.* 43(1):207-215 (2002).
Mladenovska et al., "Crosslinked gelatin microspheres containing BSA as a vaccine formulation: Biodegradation and drug release control in the presence of trypsin," *Bulletin of the Chemists and Technologists of Macedonia*, 20: 151-156 (2001).
Puri et al., "Adjuvancy enhancement of muramyl dipeptide by modulating its release from a physicochemically modified matrix of ovalbumin microspheres II. In vivo investigation," J. Controlled Release 69:69-80, 2000.
Ruegg et al., "Preparation of Proteosome-Based Vaccines. Correlation of Immunogenicity with Physical Characteristics," *J. Immunol. Methods* 135(1-2): 101-109 (1990) (abstract only).
Ryd et al., "Induction of a humoral immune response to a Shiga toxin B subunit epitope expressed as a chimeric LamB protein in a *Shigella flexneri* live vaccine strain," Microb Pathog. 12(6):399-407 (1992).
Saito et al., "Enhanced Cytosolic Delivery of Plasmid DNA by a Sulfhydryl-Activatable Listeriolysin O/protamine Conjugate Utilizing Cellular Reducing Potential," *Gene Ther.* 10(1):72-83 (2003).
Sloat and Cui., "Nasal immunization with a dual antigen anthrax vaccine induced strong mucosal and systemic immuna responses against toxins and bacilli," *Vaccine* 24: 6405-6413 (2006).
Smith, "Antibody Responses in Rabbits to Injections of Whole Cell, Flagella, and Flagellin Preparations of Cholera and Noncholera Vibrios," *Appl. Microbiol.* 27(2):375-378 (1974).
Stroffler et al., "Ribosomal proteins cross-linked to peptide chain termination release factor 2," J. Biol. Chem. 257:4203-4206, 1982.
Vella et al., "Immunogenicity of conjugate vaccines consisting of pneumococcal capsular polysaccharide types 6B, 14, 19F, and 23F and a meningococcal outer membrane protein complex," Infect. Immun. 60:4977-4983, 1992.
Wedekind et al., "Refined Crystallographic Structure of *Pseudomonas aeruginosa* Exotoxin A and its Implications for the Molecular Mechanism of Toxicity," *J. Mol. Biol.* 314:823-837, 2001.
Wong, *Chemistry of Protein Conjugation and Cross Linking* (Boca Raton, FL: CRC Press, Inc., 1993), pp. 233-243.
Wozniak et al., "His-426 of the *Pseudomonas aeruginosa* Exotoxin A is Required for ADP-Ribosylation of Elongation Factor II," *Proc. Natl. Acad. Sci. USA* 85:8880-8884, 1988.
Yu, "Development and evaluation of *Streptococcus pneumoniae* conbined vaccine," *Foreign Medical* 2:37-38 and 48 (2004).
International Search Report for International Application No. PCT/US07/17528, mailed Sep. 29, 2008.
Written Opinion for International Application No. PCT/US07/17528, mailed Sep. 29, 2008.
Supplementary European Search Report for EP 07836580.6, dated Mar. 11, 2010.
English Translation of Office Action for Japanese Patent Application No. 2009-523818, mailed Sep. 11, 2012 (3 pages).
Office Action for Japanese Patent Application No. 2009-523818, mailed Sep. 11, 2012 (4 pages).
Office Action for Japanese Application No. 2009-523818, mailed Jun. 25, 2013 (6 pages).
Office Action for Chinese Application No. 200780037545.8, dated Apr. 3, 2013 (10 pages).
Office Action for Taiwanese Patent Application No. 096128983, dated Dec. 18, 2012 (10 pages) and translation (9 pages).
Office Action for Korean Patent Application No. 10-2009-7004799, dated Oct. 25, 2013 (9 pages).
Third Office Action for Chinese Patent Application No. 200780037545.8, issued Mar. 27, 2015 (English language translation included) (9 pages).
Communication pursuant to Article 94(3) EPC for European Patent Application No. 07836580.6, dated Apr. 1, 2015 (9 pages).
First Examination Report for Indian Patent Application No. 1554/DELNP/2009, dated Mar. 27, 2014 (5 pages).
Office Action for Mexican Patent Application No. MX/a/2009/001412, mailed Jul. 15, 2014 (2 pages) (No English language translation available).
Notice of Reasons for Rejection for Japanese Patent Application No. 2013-221989, mailed Nov. 25, 2014 (English language translation provided) (9 pages).
Summons to attend oral proceedings pursuant to Rule 115(1) EPC for European Patent Application No. 07836580.6, dated Aug. 9, 2016 (9 pages).
Takamura et al., "DNA vaccine-encapsulated virus-like particles derived from an orally transmissible virsus stimulate mucosal and systemic immune responses by oral administration," Gene Ther. 11(7):628-35 (2004).

Conjugate Antigens

Figure 2

Anti-PA western blot analysis of vaccine Preps

MW DNI 1 2 3 4 5 6

220

DNI

20

Samples
1. DNI+PGA (PCMV1)
2. DNI+PGA (PCMV2)
3. DNI+PGA (PCMV3)
4. DNI+PGA without glutaraldhyde control
5. DNI only with gluaraldehydet control
6. PGA

PROTEIN MATRIX VACCINES AND RELATED METHODS OF MAKING AND ADMINISTERING SUCH VACCINES

CROSS-REFERENCE TO RELATED APPLICATIONS

This application claims benefit from U.S. provisional application Ser. No. 60/835,944, filed Aug. 7, 2006 and U.S. provisional application Ser. No. 60/933,764, filed Jun. 8, 2007, the specifications of which are hereby incorporated by reference.

STATEMENT AS TO FEDERALLY FUNDED RESEARCH

This invention was made with Government support under Grant No. U54AI057159 awarded by the National Institutes of Health (NIH). The Government has certain rights in this invention.

BACKGROUND OF THE INVENTION

The invention relates to vaccine compositions, methods of making vaccines, and methods of vaccine administration.

Many antigens, particularly those associated with a pathogen's capsule layer stimulate little or no immune response and complicate efforts to create effective vaccines against those antigens. Capsules are surface components of microbes that are typically composed of polymers of organic compounds such as carbohydrates, amino acids, or alcohols. Capsules are quite diverse chemically. The monomeric units that make up capsules (e.g., carbohydrates) can be linked together in various molecular configurations and can be further substituted with phosphate, nitrogen, sulfate, and other chemical modifications. These chemical variations allow capsules to present numerous antigenic targets on the microbial surface thus allowing escape from the host immune system directed at these targets. Capsules can also be virulence factors which prevent microbes from being phagocytosed and killed by host macrophages and polymorphoneuclear leukocytes. Antibodies against capsules provide a potent defense against encapsulated organisms by fixing complement to the microbial surface, which can result in their lysis or their opsonization, uptake, and killing by phagocytic host immune cells. The most potent antibodies against capsules are IgG antibodies. Capsules that fail to induce significant levels of IgG are called T-independent antigens. Covalent coupling of a protein to capsule renders them "T-dependent" and such antigens can elicit an IgG response.

There is a need for safe, synthetically accessible, cost-effective vaccines directed to capsule and other T-independent antigens that do not evoke strong immune responses or IgG antibody. Such vaccines are needed to protect against various infectious diseases such as infection by anthrax, pneumococcus, influenzae Type B, meningococcus, and streptococcus.

SUMMARY OF THE INVENTION

The present invention relates to vaccine compositions containing an antigen of interest entrapped with a carrier protein in a complex, methods of making such vaccines, and methods of vaccine administration.

Accordingly, in the first aspect, the invention features a vaccine composition containing an antigen of interest and a carrier protein, where (i) no more than 50% of the antigen of interest is cross-linked to the carrier protein and (ii) where the antigen is entrapped with the carrier protein to form a complex.

In desirable embodiments of the first aspect of the invention, the complex has a diameter of between 10 nm and 100 μm. In more desirable embodiments of the first aspect of the invention, the complex has a diameter of about 100 nm to 100 μm. In yet more desirable embodiments of the first aspect of the invention, the complex has a diameter of about 100 nm to 10 μm.

In other desirable embodiments of the first aspect of the invention, the complex, when administered to a mammal, elicits a T-cell dependent immune response in the mammal.

In additional desirable embodiments of the first aspect of the invention, the molar ratio of the antigen to the carrier protein is between 1 to 10 and 10 to 1. Desirably, the carrier protein is a multimer, for example, a multimer that includes at least 5 subunits. In other desirable embodiments, the multimer is a homomultimer.

In further desirable embodiments of the first aspect of the invention, the carrier protein is covalently linked to at least one other carrier protein. Desirably, the covalent linkage contains a peptide bond between a primary amino group of a lysine side chain and a carboxy group of an aspartate or glutamate side chain. In other desirable embodiments, the covalent linkage includes a compound of the formula

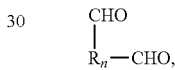

where $R_n$ is a linear or branched alkyl of 1 to 12 carbon atoms, a linear or branched heteroalkyl of 1 to 12 atoms, a linear or branched alkene of 2 to 12 carbon atoms, a linear or branched alkyne of 2 to 12 carbon atoms, an aromatic residue of 5 to 10 carbon atoms, a cyclic system of 3 to 10 atoms, $-(CH_2CH_2O)_qCH_2CH_2-$ in which q is 1 to 4, or a chemical bond linking two aldehyde groups. In additional desirable embodiments, the covalent linkage contains glutaraldehyde, m-maleimidobenzoyl-N-hydroxysuccinimide ester, carbodiimide, or bis-biazotized benzidine. In yet other desirable embodiments, the covalent linkage contains a bifunctional cross-linker. Desirably, the bifunctional cross-linker is glutaraldehyde, bis[sulfosuccinimidyl]suberate, or dimethyl adipimidate.

In other desirable embodiments of the first aspect of the invention, the carrier proteins are non-covalently linked. In desirable embodiments, the non-covalent linkage involves a hydrophobic interaction, ionic interaction, van der Waals interaction, or hydrogen bond.

In additional desirable embodiments of the first aspect of the invention, the carrier protein is diphtheria toxin or a mutant thereof, diphtheria toxoid, tetanus toxin or a mutant thereof, tetanus toxoid, Pseudomonas aeruginosa exotoxin A or a mutant thereof, cholera toxin B subunit, tetanus toxin fragment C, bacterial flagellin (e.g., Vibrio cholerae flagellin protein), pneumolysin, an outer membrane protein of Neisseria menningitidis, Pseudomonas aeruginosa Hcp1 protein, Escherichia coli heat labile enterotoxin, shiga-like toxin (e.g., Shigella SltB2 protein), human LTB protein, pneumolysin, listeriolysin O (or related proteins), a protein extract from whole bacterial cells (e.g., Pseudomonas aeruginosa or Streptococcal cells), the dominant negative mutant (DNI) of the protective antigen of Bacillus anthracis, or Escherichia coli beta-galactosidase. In particularly desirable embodiments, the carrier protein is pneumolysin, listeriolysin O, diphtheria toxin, diphtheria toxoid, tetanus toxin, or tetanus toxoid.

In other desirable embodiments of the first aspect of the invention, the antigen of interest is a polysaccharide, a polyalcohol, or a poly amino acid. Desirably, the polysaccharide contains at least 18 residues. In other desirable embodiments, the polysaccharide is a *Streptococcus pneumoniae* polysaccharide, *Francisella tularensis* polysaccharide, *Bacillus anthracis* polysaccharide, *Haemophilus influenzae* polysaccharide, *Salmonella typhi* polysaccharide, *Salmonella* species polysaccharide, *Shigella* polysaccharide, or *Neisseria meningitidis* polysaccharide. In particularly desirable embodiments, the *Streptococcus pneumoniae* polysaccharide is any one of capsular type 1-48, e.g., 3, 4, 6B, 7A, 7B, 7C, 7F, 9A, 9L, 9N, 9V, 12A, 12B, 12F, 14, 15A, 15B, 15C, 15F, 17, 18B, 18C, 19F, 23F, 25A, 25F, 33F, 35, 37, 38, 44, or 46. In other particularly desirable embodiments, the *Francisella tularensis* polysaccharide is O antigen.

In further desirable embodiments of the first aspect of the invention, the antigen of interest is a microbial capsular polymer. Desirably, the microbial capsular polymer is poly-gamma-D-glutamic acid from *Bacillus anthracis*.

In other desirable embodiments of the first aspect of the invention, the antigen of interest is an organic polymer consisting of monomers having at least three atoms, where each of the atoms is independently selected from carbon, oxygen, hydrogen, phosphate, nitrogen, and sulfate. Desirably, the organic polymer is derived from a microbe. In other desirable embodiments, the organic polymer does not occur in nature.

In additional desirable embodiments, the vaccine composition further includes a second antigen of interest. Desirably the vaccine composition further includes a third antigen of interest.

In the second aspect, the invention features a method of making a vaccine composition. This method involves (i) mixing an antigen of interest with a carrier protein to form a mixture of the antigen and the carrier protein and (ii) entrapping the antigen of interest with the carrier protein, where no more than 50% of the antigen of interest is cross-linked to the carrier protein in the vaccine composition.

In desirable embodiments of the second aspect of the invention, the vaccine composition further includes a pharmaceutically acceptable excipient.

In other desirable embodiments of the second aspect of the invention, the entrapping involves precipitating the antigen and the carrier protein from the mixture. Desirably, the precipitating involves a change in pH of the mixture, adding trichloroacetic acid (TCA) or ammonium sulfate to the mixture, changing the ionic strength of the mixture by increasing or decreasing the inorganic salt concentration of the mixture, heating the mixture to cause the carrier protein and/or the antigen to coagulate, or irradiating the mixture with sufficient flux of ionizing radiation to cause cross-linking.

In desirable embodiments of the second aspect of the invention, the molar ratio of the antigen to the carrier protein is between 1 to 10 and 9 to 10 in the vaccine composition.

In additional desirable embodiments of the second aspect of the invention, the carrier protein is a multimer. Desirably, the multimer contains at least 5 subunits. In other desirable embodiments, the multimer is a homomultimer.

In further desirable embodiments of the second aspect of the invention, the carrier proteins are non-covalently linked. Desirably, the non-covalent linkage involves a hydrophobic interaction, ionic interaction, van der Waals interaction, or hydrogen bond.

In additional desirable embodiments of the second aspect of the invention, the carrier protein is diphtheria toxin or a mutant thereof, diphtheria toxoid, tetanus toxin or a mutant thereof, tetanus toxoid, *Pseudomonas aeruginosa* exotoxin A or a mutant thereof, cholera toxin B subunit, tetanus toxin fragment C, bacterial flagellin (e.g., *Vibrio cholerae* flagellin protein), pneumolysin, listeriolysin O, an outer membrane protein of *Neisseria menningitidis, Pseudomonas aeruginosa* Hcp1 protein, *Escherichia coli* heat labile enterotoxin, shiga-like toxin (*Shigella* SltB2 protein), human LTB protein, a protein extract from whole bacterial cells (e.g., *Pseudomonas aeruginosa* or *Streptococcal* cells), the dominant negative mutant (DNI) of the protective antigen of *Bacillus anthracis*, or *Escherichia coli* beta-galactosidase. In particularly desirable embodiments, the carrier protein is pneumolysin, listeriolysin O, diphtheria toxin, diphtheria toxoid, tetanus toxin, or tetanus toxoid.

In other desirable embodiments of the second aspect of the invention, the antigen of interest is a polysaccharide, a polyalcohol, or a poly amino acid. Desirably, the polysaccharide contains at least 18 residues. In other desirable embodiments, the polysaccharide is a *Streptococcus pneumoniae* polysaccharide, *Francisella tularensis* polysaccharide, *Bacillus anthracis* polysaccharide, *Haemophilus influenzae* polysaccharide, *Salmonella typhi* polysaccharide, *Shigella* species polysaccharides, *Salmonella* species polysaccharides, or *Neisseria meningitidis* polysaccharide. In particularly desirable embodiments, the *Streptococcus pneumoniae* polysaccharide is any one of capsular type 1-48, e.g., 3, 4, 6B, 7A, 7B, 7C, 7F, 9A, 9L, 9N, 9V, 12A, 12B, 12F, 14, 15A, 15B, 15C, 15F, 17, 18B, 18C, 19F, 23F, 25A, 25F, 33F, 35, 37, 38, 44, or 46. In other particularly desirable embodiments, the *Francisella tularensis* polysaccharide is O antigen.

In additional desirable embodiments of the second aspect of the invention, the antigen of interest is a microbial capsular polymer. Desirably, the microbial capsular polymer is poly-gamma-D-glutamic acid from *Bacillus anthracis*.

In yet other desirable embodiments of the first aspect of the invention, the antigen of interest is an organic polymer consisting of monomers having at least three atoms, where each of the atoms is independently selected from carbon, oxygen, hydrogen, phosphate, nitrogen, and sulfate. Desirably, the organic polymer is derived from a microbe. In other desirable embodiments, the organic polymer does not occur in nature.

In further desirable embodiments of the second aspect of the invention, mixing in step (i) involves a second antigen of interest or even a third antigen of interest.

In the third aspect, the invention features another method of making a vaccine composition. This method involves (i) mixing an antigen of interest with a carrier protein and (ii) adding a linker that cross-links the carrier protein, where no more than 50% of the antigen of interest is cross-linked to the carrier protein in the vaccine composition.

In desirable embodiments of the third aspect of the invention, the vaccine composition further includes a pharmaceutically acceptable excipient. In other desirable embodiments of the third aspect of the invention, the molar ratio of the antigen to the carrier protein is between 1 to 10 and 10 to 1 in the vaccine composition. In additional desirable embodiments of the third aspect of the invention, the carrier protein is a multimer. Desirably, the multimer contains at least 5 subunits. In other desirable embodiments, the multimer is a homomultimer.

In further desirable embodiments of the third aspect of the invention, the method involves reducing a Schiff base in the carrier protein. In yet further desirable embodiments of the third aspect of the invention, the carrier protein is covalently linked to at least one other carrier protein. Desirably, the covalent linkage involves a peptide bond between a primary amino group of a lysine side chain and a carboxy group of an aspartate or glutamate side chain. In other desirable embodiments, the covalent linkage involves a bifunctional cross-linker. Desirably, the bifunctional cross-linker is glutaraldehyde, bis[sulfosuccinimidyl]suberate, or dimethyl adipimidate.

In additional desirable embodiments of the third aspect of the invention, the linker is a compound of the formula $$\begin{array}{c} \text{CHO} \\ | \\ R_n\text{—CHO,} \end{array}$$

where $R_n$ is a linear or branched alkyl of 1 to 12 carbon atoms, a linear or branched heteroalkyl of 1 to 12 atoms, a linear or branched alkene of 2 to 12 carbon atoms, a linear or branched alkyne of 2 to 12 carbon atoms, an aromatic residue of 5 to 10 carbon atoms, a cyclic system of 3 to 10 atoms, —$(CH_2CH_2O)_qCH_2CH_2$— in which q is 1 to 4, or a chemical bond linking two aldehyde groups.

In other desirable embodiments of the third aspect of the invention, the linker is glutaraldehyde, m-maleimidobenzoyl-N-hydroxysuccinimide ester, carbodiimide, or bis-biazotized benzidine.

In additional desirable embodiments of the third aspect of the invention, the carrier protein is diphtheria toxin or a mutant thereof, diphtheria toxoid, tetanus toxin or a mutant thereof, tetanus toxoid, *Pseudomonas aeruginosa* exotoxin A or a mutant thereof, cholera toxin B subunit, tetanus toxin fragment C, bacterial flagellin (*Vibrio cholerae* flagellin protein), pneumolysin, listeriolysin O, an outer membrane protein of *Neisseria menningitidis*, *Pseudomonas aeruginosa* Hcp1 protein, *Escherichia coli* heat labile enterotoxin, shiga-like toxin (*Shigella* SltB2 protein), human LTB protein, a protein extract from whole bacterial cells (*Pseudomonas aeruginosa* or *Streptococcal* cells), the dominant negative mutant (DNI) of the protective antigen of *Bacillus anthracis*, or *Escherichia coli* beta-galactosidase.

In further desirable embodiments of the third aspect of the invention, the antigen of interest is a polysaccharide, a polyalcohol, or a poly amino acid. Desirably, the polysaccharide contains at least 18 residues. In other desirable embodiments, the polysaccharide is a *Streptococcus pneumoniae* polysaccharide, *Francisella tularensis* polysaccharide, *Bacillus anthracis* polysaccharide, *Haemophilus influenzae* polysaccharide, *Salmonella typhi* polysaccharide, *Shigella* species polysaccharides, *Salmonella* species polysaccharides, or *Neisseria meningitidis* polysaccharide. In particularly desirable embodiments, the *Streptococcus pneumoniae* polysaccharide is any one of capsular type 1-48, e.g., 3, 4, 6B, 7A, 7B, 7C, 7F, 9A, 9L, 9N, 9V, 12A, 12B, 12F, 14, 15A, 15B, 15C, 15F, 17, 18B, 18C, 19F, 23F, 25A, 25F, 33F, 35, 37, 38, 44, or 46. In other particularly desirable embodiments, the *Francisella tularensis* polysaccharide is O antigen.

In other desirable embodiments of the third aspect of the invention, the antigen of interest is a microbial capsular polymer. Desirably, the microbial capsular polymer is poly-gamma-D-glutamic acid from *Bacillus anthracis*.

In yet other desirable embodiments of the third aspect of the invention, the antigen of interest is an organic polymer consisting of monomers having at least three atoms, where each of the atoms is independently selected from carbon, oxygen, hydrogen, phosphate, nitrogen, and sulfate. Desirably, the organic polymer is derived from a microbe. In additional desirable embodiments, the organic polymer does not occur in nature.

In further desirable embodiments of the third aspect of the invention, mixing in step (i) involves a second antigen of interest or even a third antigen of interest.

In the fourth aspect, the invention features a method of vaccinating a subject against an infectious agent. This method involves administering a vaccine composition of the first aspect of the invention to a subject in an amount sufficient to induce the production of antibodies in the subject. In desirable embodiments of the fourth aspect of the invention, the method involves a second administering step where the vaccine composition of the first aspect of the invention is administered to the subject in an amount sufficient to boost the production of antibodies in the subject. Desirably, in the fourth aspect of the invention, the production of antibodies is T-cell dependent. In other desirable embodiments of the fourth aspect of the invention, the production of antibodies is sufficient to prevent or reduce infection of the subject by an infectious agent. Desirably, the infectious agent is pneumococcus, meningococcus, *Haemophilus influenzae* type B, *Pseudomonas aeruginosa*, *Francisella tularensis*, *Shigella* species, *Salmonella* species, *Acinetobacter* species, *Burkholderia* species, or *Escherichia coli*.

In other desirable embodiments of the fourth aspect of the invention, the method involves a second administering step where a second vaccine composition containing an antigen of interest is provided to the subject in an amount sufficient to boost the production of antibodies in the subject. Desirably, the production of antibodies is sufficient to prevent or reduce infection of the subject by a second infectious agent.

In desirable embodiments of the fourth aspect of the invention, the antibodies are IgG antibodies. In a further desirable embodiment of the fourth aspect of the invention, the subject is a human.

In desirable embodiments of any one of the aspects of the invention, the *Streptococcus pneumoniae* polysaccharide is one of capsular types described in Kong et al. (J. Med. Microbiol. 54:35-356, 2005). For example, the *Streptococcus pneumoniae* polysaccharide capsular type desirably is 1 (e.g., 1-g or 1-q), 2 (e.g., 2-g, 2-q, or 2-41A), 3 (e.g., 3-g, 3-q, 3-c, or 3-nz), 4, 5 (e.g., 5-q, 5-c, 5-qap, or 5-g), 6A (e.g., 6A-g, 6A-c1, 6A-c2, 6A-n, 6A-qap, 6A-6B-g, 6A-6B-q, or 6A-6B-s), 6B (e.g., 6B-c, 6A-6B-g, 6A-6B-q, or 6A-6B-s), 7F (e.g., 7F-7A), 7A (e.g., 7A-cn or 7F-7A), 7B (e.g., 7B-40), 7C (e.g., 7C-19C-24B), 8 (e.g., 8-g or 8-s), 9A (e.g., 9A-9V), 9L, 9N, 9V (e.g., 9A-9V), 9V and 14, 10F (e.g., 10E-q, 10E-ca, or 10E-10C), 10A (e.g., 10A-17A or 10A-23F), 10B (e.g., 10B-10C), 11F, 11A (e.g., 11A-nz or 11A-11D-18F), 11B (e.g., 11B-11C), 11C (e.g., 11B-11C or 11C-cn), 11D (e.g., 11A-11D-18F), 12F (e.g., 12F-q or 12F-12A-12B), 12A (e.g., 12A-cn, 12A-46, or 12F-12A-12B), 12B (e.g., 12F-12A-12B), 13 (e.g., 13-20), 14 (e.g., 14-g, 14-q, 14-v, or 14-c), 15F (e.g., 15F-cn1 or 15F-cn2), 15A (e.g., 15A-ca1, 15A-ca2, or 15A-chw), 15B (e.g., 15B-c, 15B-15C, 15B-15C-22F-22A), 15C (e.g., 15C-ca, 15C-q1, 15C-q2, 15C-q3, 15C-s, 15B-15C, or 15B-15C-22F-22A), 16F (e.g., 16F-q or 16F-nz), 16A, 17F (e.g., 17F-n and 17F-35B-35C-42), 17A (e.g., 17A-ca or 10A-17A), 18F (e.g., 18F-ca, 18F-w, or 11A-11D-18F), 18A (e.g., 18A-nz or 18A-q), 18B (e.g., 18B-18C), 18C (e.g., 18B-18C), 19F (e.g., 19F-g1, 19F-g2, 19F-g3, 19F-q, 19F-n, or 19F-c), 19A (e.g., 19A-g, 19A-, or 19A-ca), 19B, 19C (e.g., 19C-cn1, 19C-cn2, or 7C-19C-24B), 20 (e.g., 13-20), 21 (e.g., 21-ca or 21-cn), 22F (e.g., 15B-15C-22F-22A), 23F (e.g., 23F-c, 10A-23F, or 23F-23A), 23B (e.g., 23B-c or 23B-q), 24F (e.g., 24F-cn1, 24F-cn2, or 24F-cn3), 24A, 24B (e.g., 7C-19C-24B), 25F (e.g., 25F-38), 25A, 27, 28F (e.g., 28F-28A or 28F-cn), 28A (e.g., 28F-28A), 29 (e.g., 29-ca or 29-q), 31, 32F (e.g., 32F-32A), 32A (e.g., 32A-cn or 32F-32A), 33F (e.g., 33F-g, 33F-q, 33F-chw, 33F-33B, or 33F-33A-35A), 33A (e.g., 33F-33A-35A), 33B (e.g., 33B-q, 33B-s, or 33F-33B), 33D, 34 (e.g., 34-ca or 34s), 35F (e.g., 35F-47F), 35A (e.g., 33F-33A-35A), 35B (e.g., 17F-35B-35C-42), 36, 37 (e.g., 37-g or 37-ca), 38 (e.g., 25F-38), 39 (e.g., 39-cn1 or 39-cn2), 40 (e.g., 7B-40), 41F (e.g., 41F-cn or 41F-s), 41A (e.g., 2-41A), 42 (e.g., 17B-35B-35C-42), 43, 44, 45, 46 (e.g., 46-s or 12A-46), 47F (e.g., 35F-47F), 47A, 48 (e.g., 48-cn1 or 48-cn2), or GenBank Accession Number AF532714 or AF532715.

DEFINITIONS

By "administering" as used herein in conjunction with a vaccine, is meant providing to a subject a vaccine in a dose sufficient to induce an immune response in the subject, where the immune response results in the production of antibodies that specifically bind an antigen contained in the vaccine. Administering desirably includes intramuscular injection, intradermal injection, or transcutaneous injection and, desirably involves administration of appropriate immune adjuvants. Administering may involve a single administration of a vaccine or administering a vaccine in multiple doses. Desirably, a second administration is designed to boost production of antibodies in a subject to prevent infection by an infectious agent. The frequency and quantity of vaccine dosage depends on the specific activity of the vaccine and can be readily determined by routine experimentation.

By "cross-link" is meant the formation of a covalent bond between two molecules, macromolecules, or combination of molecules, e.g., carrier proteins, either directly, when a "zero-length" linker is used, or by use of third molecule, the chemical linker, that has two functional groups each capable of forming a covalent bond with one of two separate molecules or between two separate groups in the same molecule (i.e., these would form "loops" that could also wrap around the polymer). Exemplary linkers include bifunctional linkers which are capable of cross-linking two carrier proteins. Cross-linking may also occur between an antigen and a carrier protein.

By "antigen" as used herein is meant is any molecule or combination of molecules that is specifically bound by an antibody or an antibody fragment.

By "bifunctional linker" as used herein is meant a compound that has two functional groups each separately capable of forming a covalent bond with two separate molecules, atoms, or collections of molecules. Exemplary bifunctional linkers are described, for example, by G. T. Hermanson (Bioconjugate Techniques, Academic Press, 1996) and Dick and Beurret (Conjugate Vaccines. Contribu. Microbiol. Immunol., Karger, Basal 10:48-114, 1989). Desirably a bifunctional linker is glutaraldehyde, bis[sulfo-succinimidyl]suberate, or dimethyl adipimidate.

By a "linker" as used herein is meant a compound or a chemical bond that covalently joins two or more molecules. Desirably a linker is glutaraldehyde or a compound of the formula

where $R_n$ is a linear or branched alkyl of 1 to 12 carbon atoms, a linear or branched heteroalkyl of 1 to 12 atoms, a linear or branched alkene of 2 to 12 carbon atoms, a linear or branched alkyne of 2 to 12 carbon atoms, an aromatic residue of 5 to 10 carbon atoms, a cyclic system of 3 to 10 atoms, $-(CH_2CH_2O)_qCH_2CH_2-$ in which q is 1 to 4, or a chemical bond linking two aldehyde groups. Linking may be direct without the use of a linking molecule. For example, a protein's carboxyl group may be linked directly to its amino group using carbodiimide chemistry or enymatically using transglutamidases which catalyze cross-linking of this sort.

By "boost the production of antibodies" is meant the activation of memory B-cells that occurs during a second exposure to an antigen, called a "booster response," and is indicative of a long lived "secondary" memory immune response, resulting in the long lived production of antibodies.

By "carrier protein" is meant a protein used in a vaccine that invokes an immune response to itself and/or to an antigen complexed with a carrier protein. Desirably the antigen is non-covalently associated with the carrier protein by being entrapped in a complex with the carrier protein. Nonetheless, the antigen and the carrier protein may also be covalently linked to each other. Desirably, the carrier protein contains an epitope recognized by a T-cell. Also encompassed by the definition of a "carrier protein" are multi-antigenic peptides (MAPs), which are branched peptides. Desirably, a MAP includes lysine. Exemplary desirable carrier proteins include toxins and toxoids (chemical or genetic), which may be mutant. Desirably, a carrier protein is diphtheria toxin or a mutant thereof, diphtheria toxoid, tetanus toxin or a mutant thereof, tetanus toxoid, Pseudomonas aeruginosa exotoxin A or a mutant thereof, cholera toxin B subunit, tetanus toxin fragment C, bacterial flagellin, pneumolysin, listeriolysin O (and related molecules), an outer membrane protein of Neisseria menningitidis, Pseudomonas aeruginosa Hcp1 protein, Escherichia coli heat labile enterotoxin, shiga-like toxin, human LTB protein, a protein extract from whole bacterial cells, the dominant negative mutant (DNI) of the protective antigen of Bacillus anthracis, or Escherichia coli beta-galactosidase, or any other protein that can be cross-linked by a linker.

By "DNI" is meant the dominant negative mutant (DNI) protein, which is a mutated form of protective antigen (PA) of B. anthracis, as described by Benson et al. (Biochemistry 37:3941-3948, 1998).

By "entrapped" as used herein in reference to an antigen is meant an antigen that remains in a complex with carrier proteins under physiological conditions. Desirably, the antigen is entrapped in a complex with carrier proteins in the absence of significant covalent bonding between the antigen and a carrier protein. Absence of significant covalent bonding, as used herein, refers to no more than 50% of the antigen being covalently bonded to a carrier protein. Desirably, no more than 40%, 30%, 10%, or 5% of the antigen is covalently bonded to a carrier protein.

By "infection" is meant the invasion of a subject by a microbe, e.g., a bacterium, fungus, parasite, or virus. The infection may include, for example, the excessive multiplication of microbes that are normally present in or on the body of a subject or multiplication of microbes that are not normally present in or on a subject. A subject is suffering from a microbial infection when an excessive amount of a microbial population is present in or on the subject's body or when the presence of a microbial population(s) is damaging the cells or causing pathological symptoms to a tissue of the subject.

By "infectious agent" is meant a microbe that causes an infection.

By "immunogenic" is meant a compound that induces an immune response, in a subject. Desirably, the immune response is a T-cell dependent immune response that involves the production of IgG antibodies.

By "microbe" is meant a bacterium, fungus, parasite, or virus that is capable of causing an infection in a subject.

By "microbial capsular polymer" is meant a polymer present in or on the capsule coating of a microbe. Desirably, a microbial capsular polymer is an organic polymer such as a polysaccharide, phosphopolysaccharide, polysaccharide with an amino sugar with a N-acetyl substitution, polysaccharide containing a sulfanylated sugar, another sulfate-modified sugar, or phosphate-modified sugar, polyalcohol, poly amino acid, teichoic acid, and an O side chain of a lipopolysaccharide.

By "monomer" is meant a molecular structure capable of forming two or more bonds with like monomers, often yielding a chain or a series of branched, connected chains of repeating monomer substructures, when part of a "polymer."

By "organic polymer" is meant a polymer composed of covalently linked monomers each having three or more of the following atoms: carbon, oxygen, hydrogen, phosphate, nitrogen, and sulfate. Desirably, an organic polymer is a polysaccharide, phosphopolysaccharide, polysaccharide with an amino sugar with a N-acetyl substitution, polysaccharide containing a sulfanylated sugar, another sulfate-modified sugar, or phosphate-modified sugar, sugar, polyalcohol, polyamino acid, teichoic acid, and an O side chain of lipopolysaccharide.

By "polyalcohol" is meant a hydrogenated form of a carbohydrate where a carbonyl group has been reduced to a primary or secondary hydroxyl group. Exemplary polyalcohols are a polyalkylene oxide (PAO), such as a polyalkylene glycols (PAG), including polymethylene glycols, polyethylene glycols (PEG), methoxypolyethylene glycols (mPEG) and polypropylen glycols; poly-vinyl alcohol (PVA); poly-ethylene-co-maleic acid anhydride; polystyrene-co-malic acid anhydride; dextrans including carboxymethyl-dextrans; celluloses, including methylcellulose, carboxymethylcellulose, ethylcellulose, hydroxyethylcellulose carboxyethylcellulose, and hydroxypropylcellulose; hydrolysates of chitosan; starches such as hydroxyethyl-starches and hydroxy propyl-starches; glycogen; agaroses and derivates thereof; guar gum; pullulan; inulin; xanthan gum; carrageenan; pectin; alginic acid hydrolysates; sorbitol; an alcohol of glucose, mannose, galactose, arabinose, gulose, xylose, threose, sorbose, fructose, glycerol, maltose cellobiose, sucrose, amylose, amylopectin; or mono propylene glycol (MPG).

By "poly amino acid" is meant at least two amino acids linked by a peptide bond. Desirably, a poly amino acid is a peptide containing a repetitive amino acid sequence or a chain of the same amino acid (i.e., a homopolymer).

By "reducing a Schiff base" is meant exposing azomethine or a compound of the formula $R_1R_2C=N-R_3$ (where $R_1$, $R_2$, and $R_3$ are chemical substructures, typically containing carbon atoms) to a reducing agent that saturates the double bond of the Schiff base with hydrogen atoms. Methods of reducing are known to those skilled in the art.

By "specifically binds" as used herein in reference to an antibody or a fragment thereof, is meant an increased affinity of an antibody or antibody fragment for a particular protein, e.g., an antigen, relative to an equal amount of any other protein. An antibody or antibody fragment desirably has an affinity for its antigen that is least 2-fold, 5-fold, 10-fold, 30-fold, or 100-fold greater than for an equal amount of any other antigen, including related antigens, as determined using standard methods such as an enzyme linked immunosorbent assay (ELISA).

By "subject" is meant an animal that can be infected by a microbe. Desirably, a subject is a mammal such as a human, monkey, dog, cat, mouse, rat, cow, sheep, goat, or horse. In a desirable embodiment, the subject is a human, such as a human child. Desirably, the subject is a human infant, toddler, or pre-pubescent child.

By "T-cell independent antigen" is meant an antigen which results in the generation of antibodies without the cooperation of T lymphocytes. The T-cell independent antigen desirably directly stimulates B lymphocytes without the cooperation of T lymphocytes. Exemplary desirable T-cell independent antigens include capsular antigen poly-gamma-D-glutamic acid (PGA), alginic acid (algenate), dextran, polysaccharides (PS), poly amino acids, polyalcohols, and nucleic acids.

ADVANTAGES

Compared to existing vaccine technologies, the vaccines of the present invention are simple to make, less prone to chemical problems, less prone to immunological problems, less expensive, more adaptive to different antigens of interest and carrier proteins than conjugate technology, and more flexible for creating multivalent vaccines (vaccines protective against multiple antigens).

The vaccines of the present invention do not require covalent linkage between a carrier protein and the antigen intended to evoke an immune response, thus simplifying the method of making them and reducing the cost of their preparation compared to conjugate vaccine technology. Polysaccharide (PS)-protein conjugate vaccines have been prohibitively expensive to produce and sell in the developing world; conventional conjugate vaccines are difficult to produce cheaply because of the highly specialized chemistry required for each vaccine and the costs of production and purification of both PS and carrier protein.

The vaccines of the present invention also address a need for vaccines that can safely induce immunity against previously intractable antigens. Such vaccines may be monovalent (having single antigens to induce an immune response) or multivalent (having multiple antigens to induce multiple immune responses). Vaccines containing TLR (Toll-like receptor) ligands have been shown to evoke immune responses for otherwise intractable antigens, but they tend to be unsafe because TLR ligands are often proinflammatory, toxic in even small doses, reactogenic, and likely to cause adverse symptoms compared to vaccines of the invention.

Other features and advantages of the invention will be apparent from the following Detailed Description, the drawings, and the claims.

BRIEF DESCRIPTION OF THE DRAWINGS

FIG. 2 is an image of Western blot analysis of PCMV and control preparations monitored for cross-linking by SDS polyacryamide gel electrophoresis and Western blotting with anti-PA antiserum. DNI protein migrates at 84 kDa before glutaraldehyde cross-linking. PCVM1-PCMV3 (lanes 1-3) show extensive cross-linking of the DNI protein as evidenced by the migration of bands at molecular masses greater than 220 kDa. DNI protein alone cross-linked in the absence of PGA also shows the same high molecular weight species (lane 5). In contrast, DNI mixed with PGA but not treated with glutaraldehyde shows bands that co-migrate with DNI or lower molecular weight species (lane 4).

Figure 1:
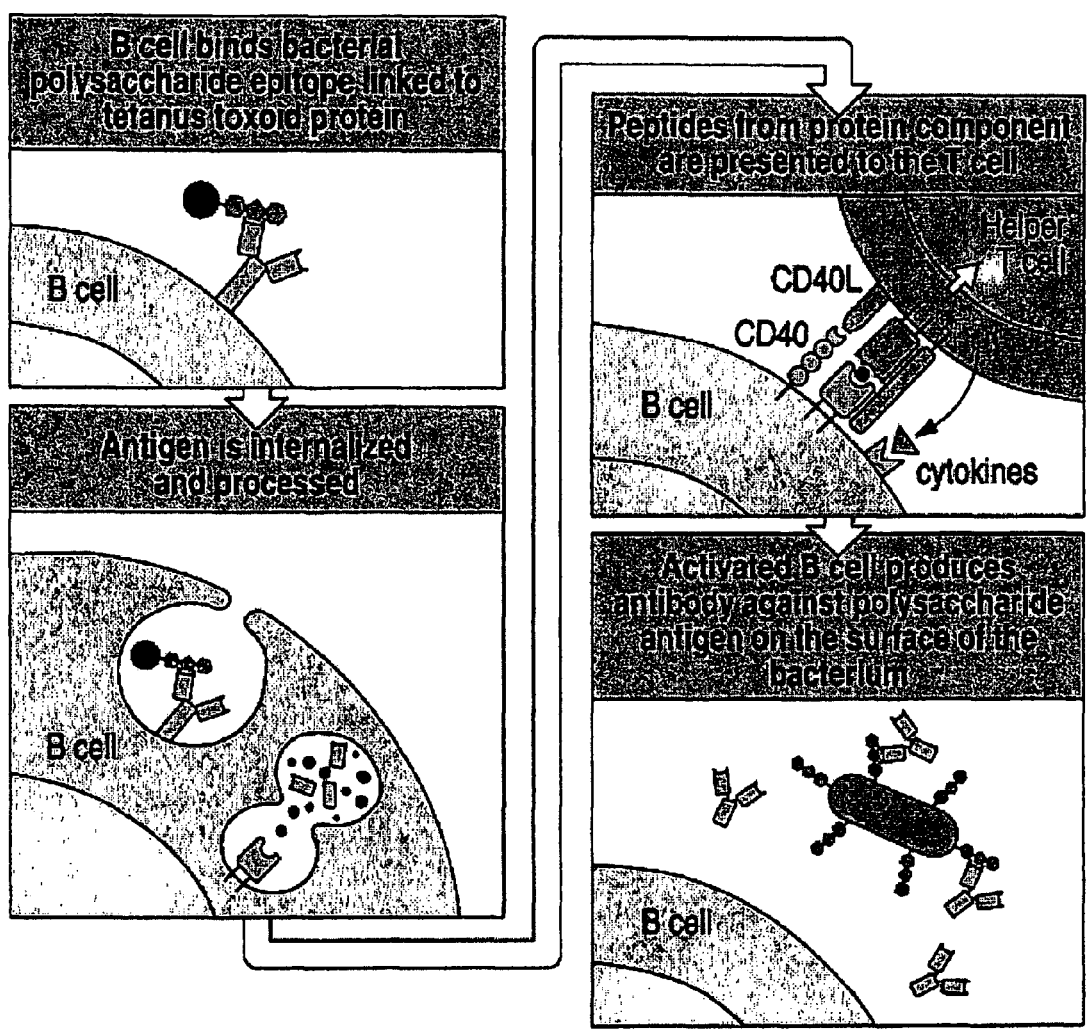
FIG. 1 is a schematic diagram of a non-limiting proposed pathway for the induction of an anti-PS IgG immune response by a conjugate vaccine for a conjugate made between a PS and the carrier protein tetanus toxoid. In this model, only B-cells that display antibody receptors that recognize the PS bind the PS-protein conjugate. Thus, the carrier protein is bound to the surface of the B-cell that displays the correct PS binding specificity.

FIG. 12 is a graph showing that PCMVs containing pss 6B are as effective as Prevnar® at inducing IgM production.

FIG. 13 is a graph showing that PCMVs containing pss 6B are more effective at inducing IgG production than Prevnar®.

FIGS. 14-16 are graphs showing that PCMVs containing pss 14 are approximately equivalent to Prevnar® at inducing IgG production (DTx=Diphtheria toxoid; TTx=Tetanus toxoid).

DETAILED DESCRIPTION

The invention features vaccine compositions and methods of making and administering such compositions to provide immunity against T-cell independent antigens or antigens which normally invoke weak immune responses, such as, e.g., polysaccharides (PS), polyalcohols, poly amino acids, and other organic polymers. The vaccines of the invention have the potent immunological properties of typical PS-protein conjugate vaccines but desirably differ from conjugate vaccines in that no significant covalent atomic bonding is required to couple the antigen of interest, e.g., PS or capsular organic polymer, to the carrier protein. Rather, the antigen of interest, e.g., PS or capsular organic polymers, is entrapped with the carrier protein. For example, a protein matrix may be formed by covalent cross-linking carrier protein molecules to themselves in the presence of soluble antigen, e.g., PS or capsular organic polymers: these vaccines are referred to as protein matrix vaccines. Carrier proteins that are highly cross-linked to each other can from a matrix that can capture an antigen and facilitate the uptake of that antigen and the stimulation of antibody production in immune cells. The carrier protein matrix may be in the form of a "mesh" that encloses the antigen or a series of "beads on a string" where the antigen is the "string", the protein or complexes of cross-linked proteins is the "bead" in this analogy. The antigen is entrapped with the carrier protein if the carrier protein encircles the antigen to form a ring around the antigen or a 3-dimensional mesh in which the antigen is tangled within. Also, the carrier and the antigen may be cross-linked, for instance, by intra-chain cross-links in the antigen chain with the carrier protein. In desirable embodiments, the antigen and the carrier protein are non-covalently linked. Such non-covalent linkage may involve a hydrophobic interaction, ionic interaction, van der Waals interaction, or hydrogen bond. Non-covalent linkage can include physical geometric configurations that non-covalently associate antigen with protein complexes (see: "bead on a string" analogy above).

The carrier protein need not be cross-linked to itself to entrap an antigen. An antigen can also be entrapped by, for example, mixing the carrier protein and the antigen in an aqueous solution and precipitating the carrier protein, thereby co-precipitating the antigen with the protein. An antigen may also be entrapped with a carrier protein by precipitating a compound (e.g., alum, sodium hexametaphosphate, polyphosphazene, or other polymers with affinity for proteins driven by hydrophobic or ionic interactions) from a mixture of antigen and carrier protein. Methods of precipitating proteins are standard in the art and include, for example, (1) changing the pH of the mixture, (2) changing the ionic strength of the solution by increasing or decreasing inorganic salt concentration of the mixture, (3) or adding trichloroacetic acid (TCA) or ammonium sulfate to the mixture, (4) heating the mixture to cause the protein to coagulate (i.e., form a precipitate or gel), (5) chemically modifying the protein in the mixture in a way that renders it insoluble, and (6) irradiating the protein solution with a sufficient flux of ionizing radiation (ultraviolet, gamma, or beta rays) as to cause cross-linking and/or precipitation of the protein, among others.

When a capsular protein of a pathogen is used, such vaccines are termed protein capsular matrix vaccines (PCMV). As described in the Examples, PCMVs were produced including ones based on the model T-independent capsular antigen, poly-gamma-D-glutamic acid (PGA), as well as alginic acid (algenate) and dextran, and the exemplary carrier protein, DNI. The PGA PCMV was simple to make in large quantity and was found to induce immune responses typical of PGA-protein conjugate vaccines. Vaccines of the invention may be prepared using any of many possible linkers to cross-link any of many possible carrier proteins in the presence of any antigen of interest. Exemplary and preferred linkers, carrier proteins, and antigens of interest are discussed herein.

Polysaccharides (PS) are polymers of saccharides (sugars). PS derived from capsules are the primary antigenic components involved in protective immunity against encapsulated bacterial pathogens such as *Neisseria meningitidis*, *Streptococcus pneumoniae*, *Salmonella typhi*, and *Haemophilus influenzae* Type B. Immunization of adolescents and adults with vaccines based on microbial PS has been successful in reducing disease burden, but has proven less effective in providing protective immunity to infants and young children (i.e., children less than 24 months of age). Young children have not yet developed a mature adaptive immune repertoire and T cell-independent antigens such as capsular PS are poorly immunogenic and do not lead to long-term protective immune responses (i.e., an immunological memory response) in such young vaccine recipients.

A T-cell independent antigen such as PS can be converted to a T-cell dependent antigen by chemical coupling of PS to protein; this process is called "conjugation" and involves the formation of covalent bonds between atoms in the PS structure and side chain atoms of amino acids present in the "carrier" protein. Such "conjugate vaccines" more efficiently promote the induction of B-cell maturation and isotype switching leading to much higher levels of antibody with the correct anti-PS protective profile. Protective antibodies have high affinity for their PS antigens, and typically are of the Immunoglobulin G (IgG) subclass, a long-lived antibody with complement fixing and opsonic effector activity.

An exemplary, non-limiting pathway for induction of an anti-PS IgG immune response by a conjugate made between a PS and the carrier protein tetanus toxoid is shown in FIG. 1. In this model, only B-cells that display antibody receptors that recognize the PS bind the PS-protein conjugate. Thus, the carrier protein is bound to the surface of the B-cell that displays the correct PS binding specificity. The protein-PS complex is taken up by these B-cells into the intracellular vacuolar compartment where the carrier is processed by proteolytic degradation. Peptides derived from the carrier protein are transported and loaded into the presentation groove of the MHC-Class II receptor (MHC-II). This MHC-II-carrier peptide complex is displayed on the surface of the B-cell. Upon recognition of the MHC-II-peptide complex by the T-cell receptor (TCR), T-cells become activated and secrete cytokines that provide "help" for the induction of B-cell differentiation. B-cells expand in numbers and differentiate into "plasma cells" which now secrete antibody. Initially Immunoglobulin M (IgM) is produced by plasma cells but eventually the T-cell help causes the plasma cells to class switch and produce other isotype classes of antibody such as IgG. This process continues with plasma cells undergoing mutational changes leading to production of antibody receptors that have even higher affinity for the PS-protein conjugates. As antigen is cleared, only the higher affinity plasma cells are activated by residual PS-protein conjugate remaining in circulation. The process of T-cell dependent maturation of plasma cells continues, leading to the expansion of plasma cell populations which produce high affinity antibodies of the IgG class. The expansion can be easily monitored by measuring the levels of anti-PS IgG antibodies in the serum of an immunized subject, e.g., a human.

Eventually the maturation and switching process leads to the production of Memory B-cells which are long lived and specific for the PS. Memory B-cells have a unique property in that they can be immediately activated if exposed to PS. Activation causes Memory B-cells to multiply and quickly produce anti-PS IgG. The activation of memory B cells that occurs during a second exposure of to PS antigen is called a "booster response" and is indicative of a long lived "secondary" memory immune response. Primary immunization may stimulate the production of IgM antibodies and some IgG antibodies. Upon secondary immunization, i.e., the "booster" shot, memory cells already programmed by the first immunization are stimulated to produce large quantities of IgG, the memory immune response.

A T-cell independent antigen generally does not stimulate lasting immunity, i.e., the production of IgG antibodies, but may stimulate the production of less potent and more temporary IgM antibodies. As such, PS antigens alone do not typically produce booster responses of IgG. However, PS do produce booster responses if primary immunization is performed with a PS-protein conjugate because memory cells induced by the conjugate have already been programmed to produce IgG. Indeed, the booster response in vaccinated animals or humans is thought to mimic the protective response due to exposure to a microbe displaying the PS; this long term memory is critical for a vaccine to work in protecting immunized subjects years after their immunization with conjugate vaccines. Thus, PS-protein conjugates are valued for (1) their ability to induce high levels of IgG against PS antigens, and (2) their ability to induce memory immune responses against PS antigens. PS antigens typically do not display these properties and thus are inferior antigens. The difficulty in synthesizing conjugate vaccines and their cost of production has slowed the development of conjugate vaccines for many bacterial diseases where an immune response to PS may be protective.

Other T-cell independent antigens include homopolymers of amino acids, such as poly-gamma-D-glutamic acid (PGA), and polyalcohols. Indeed most biological polymers are T-cell independent antigens. Polymers can crosslink Immunoglobulin (Ig) receptors on B-cells that recognize them due to the repetitive nature of their chemical structures (and thus epitopes). Thus polymers can activate B-cells for production of anti-polymer IgM in the same way that polysaccharides do. For example, an amino acid homopolymer, poly-gamma-D-glutamic acid (PGA) of *Bacillus anthracis*, is a capsular polymer that is poorly immunogenic and also a T-cell independent antigen. Vaccines composed of PGA conjugated to protein carriers are highly immunogenic, able to induce anti-PGA IgG, and immunological memory to PGA. Hence, most polymers respond like PS in terms of their immunogenicity because they cannot be processed and displayed in the context of MHC-II and thus cannot recruit T-cell help. An exception is found in some naturally-occurring polymers that interact with another class of receptor termed Toll-like receptors (TLRs). Once activated, TLRs can induce production of cytokines by host cells and produce changes in the adaptive immune response. Some PS are covalently attached to TLR ligands or contaminated with such ligands. For example, lipopolysaccharides (LPS) are PS that are highly immunogenic and induce IgG and memory responses; the lipid A moiety of LPS is a TLR ligand and may be responsible for the immunological properties.

In another example, a few pneumococcal PS have been found to display some of the immunological properties of conjugate vaccines in that they induce isotype switching to IgG even if they are not attached to a protein carrier. Recently, the commercial polysaccharide vaccine Pneumovax-23, as well as individual PS from various strains of *Streptococcus pneumoniae*, were found to be contaminated with TLR ligands (Sen et al., J. Immunol. 175:3084-3091, 2005). This finding may explain why these PS preparations can induce isotype switching to IgG in the absence of protein conjugation. These pneumococcal PS induced IL-6 and TNF-α secretion by macrophages. However, further purification of the PS by phenol extraction abrogated cytokine secretion from macrophages. In immunization studies, the phenol extracted PS were poorly immunogenic and no longer induced an anti-PS IgG. Thus, phenol extraction removes contaminating molecules that were responsible for these unusual immunogenic properties of this PS preparation. The contaminating molecules appear to be TLR ligands given their ability to activate TLR-dependent cytokine responses in macrophages. Further purification of the PS by phenol extraction removed the contaminating TLR ligands and rendered the PS totally T-cell independent.

The above example illustrates that PS antigen can act like conjugate PS-protein antigens without covalent coupling of protein to carbohydrate. Unfortunately, TLR ligands are usually proinflammatory. For example, LPS is toxic in even small doses. Thus, while mixing a TLR ligand with a PS might broaden the immune response to the PS, this approach is also likely to produce vaccine that is reactogenic and likely to cause adverse symptoms in vaccine recipients. Conjugate vaccine technology remains the method of choice for production of PS vaccine with the desired spectrum of immunogenicity and safety.

The development of PS-protein conjugate vaccines has greatly reduced the childhood disease burden caused by invasive bacterial pathogens. A handful of such vaccines including ones against *Haemophilus influenzae* Type B and certain strains of meningococci and streptococci are commercially available in the developed world. These PS-protein conjugate vaccines are prohibitively expensive to produce and sell in the developing world. For example, the commercially available 7-valent pneumococcal conjugate vaccine costs about $58 (2006 U.S. dollars) per dose and requires a four-dose regimen. The cost alone puts this vaccine out of the reach of those in developing countries that carry the burden of the disease.

Conventional conjugate vaccines are difficult to produce cheaply because of the chemistry involved and the costs of production and purification of both PS and carrier protein. Usually both need to be quite pure before conjugation chemistry can be performed with a reasonable coupling efficiency. Typically, coupling chemistry must be worked out for various PS that is unique for the chemistry of the PS and the carrier proteins that have been selected. This coupling chemistry introduces functional groups in the PS that then can be linked to carrier protein typically through the epsilon amino side chains of lysine residues. The chemical modification of PS to introduce such coupling groups can destroy epitopes on the PS and introduce new epitopes (e.g., associated with the linker or modified saccharide groups) whose significance can only be assessed by performing careful immunological analysis. Furthermore, for conventional PS-protein conjugate vaccines, the size of the PS, the number of PS molecules bound per protein carrier molecule, the nature of the carrier selected, and the type of linkage chemistry can all affect immunogenicity of the conjugate vaccine. As such, for example, in the case of pneumococcal disease where each of the 90+ known serotypes has a different PS structure (Bentley et al., PLOS Genetics 2(3):e31 262-269, 2006), one single conjugation method may not be appropriate for all serotypes. Reproducibly synthesizing conjugate vaccines with reproducible immunological properties involves careful control of the size of the PS, the number of PS molecules bound per protein carrier molecule, the nature of the carrier selected, and the type of linkage chemistry and this, in turn, dramatically increases the cost of manufacture of conjugate vaccines.

The emergence of antibiotic resistance highlights the urgency for the development of safe and effective vaccines. Making vaccines widely available, especially for those in developing countries, requires that the manufacture of vaccines also to be cost-effective. Incorporation of combined conjugate vaccines against many polysaccharide antigens from different serotypes of one or more bacterial species into the childhood immunization regimen would simplify vaccine administration in that high-risk population. However, current conjugate vaccine technology is not cost-effective and thus, combination conjugate vaccines are virtually impossible to deliver to the developing world. Indeed even in the developed world with its strong established markets, the recent supply shortage of the Wyeth 7-valent conjugate pneumococcal vaccine illustrates how difficult it is to produce and stockpile a vaccine that requires complex conjugate vaccine synthetic technology.

In desirable embodiments, the vaccines of the invention are polyvalent capsular matrix vaccines (PCMV) where one or more bacterial capsular components are entrapped in a polyvalent carrier protein matrix. PCMVs can be produced easily because one needs as a starting material the antigen of interest, e.g., capsules, that are only moderately pure. For example, Vedan poly gamma-D-glutamic acid (PGA) is not pure (it carried a protease active on DNI) yet, as described herein, it performed exactly as expected for a T-cell independent antigen (Example 1). Incorporation of PGA into a PCMV was successful in all three PCMV preparations that varied in their protein-to-PGA ratios over a 7-fold range.

Because the method of making vaccines of the invention does not require any knowledge of the chemistry of the antigen of interest, e.g., the capsule polysaccharide, the method does not depend on the need to develop cross-linking chemistry that is compatible with the chemistry of the antigen of interest and the carrier protein. While it is possible that some antigens may nonetheless interact with the linker, this should not detract from the efficacy of the vaccine, because the unintended cross-linking of the antigen of interest and the carrier protein would be expected to have immunogenic properties anyway. In the vaccines of the invention, cross-linking of the antigen of interest to the carrier protein is not a requirement for the vaccine to be effective. This is in sharp contrast to conventional conjugate vaccines, which are thus hampered in their manufacture and development. The vaccines of the invention desirably have at least, e.g., 1%, 5%, 10%, 20%, 30%, 40%, 50%, 60%, 70%, 80%, 90%, 95%, 98%, or even 100% of the carrier proteins cross-linked and no more than, e.g., 1%, 5%, 10%, 15%, 20%, 30%, 40%, 50%, 60%, 70%, 80%, or 90% of the antigen of interest is cross-linked to the carrier protein. Desirably, no more than 10% of antigens are cross-linked to the carrier proteins and at least 50% of carrier proteins are cross-linked.

The methods of making vaccines described herein do not result in the extensive modification of the antigen of interest, e.g., a capsular polymer. The antigen generally remains in the same state with a possible modification being, e.g., the reduction of reducing sugars for PS capsules that carry such groups at the end of the polymer chains. Such minor modifications are unlikely to affect immunogenicity of most capsular PS because the end sugars are 100-1000× less abundant than the internal residues in the polymer. In contrast, for conventional conjugate vaccines, it is usually necessary to introduce linker groups into the antigen, e.g., a capsular polymer, that serve as the point of covalent attachment of the carrier protein. Linkers need to be used because many antigens, e.g., capsular polymers, do not have a reactive group such as a carboxyl or amino group as part of their structure. For example, the introduction of linker chemistry into a PS can result in destruction of capsular epitopes and generation of novel epitopes that might be undesirable in a vaccine product because of their unknown immunological cross-reactivity with host self-epitopes.

The methods of making vaccines described herein are less complex than conjugate vaccine technology because its chemistry depends only on the cross-linking chemistry of the carrier protein (e.g., DNI, cholera toxin B subunit, diphtheria toxin, tetanus toxin Fragment C, or *Escherichia coli* beta-galactosidase). For example, while the capsular polymer affects the rate of cross-linking when mixed with DNI, it does not affect the pattern or extent of cross-linking which is governed more by the protein being used, its concentration, and the concentration of the cross-linking agent (e.g., glutaraldehyde) added. These parameters can readily be adjusted, thereby reducing the time and effort required to make the vaccine, and saving expense.

The methods of making PCMV vaccines described herein can be used with any antigen, e.g., any capsular polymer or any polymer with few if any amino groups, and any carrier protein that can be cross-linked, e.g., carrier proteins not having critical epitopes that can be destroyed by borohydride reduction. Carrier proteins that may be used in the methods described herein desirably have at least 2 lysine residues or other residues that are unblocked and that can be cross-linked by chemical modification. Tetanus toxoid is one possible carrier protein. This toxin is detoxified by treatment with formaldehyde, a reagent that reacts with amino groups of proteins. Other desirable carrier proteins include the cholera toxin B subunit (available from SBL Vaccin AB), diphtheria toxin, tetanus toxin Fragment C (available from Sigma Aldrich), DNI, or beta-galactosidase from *Escherichia coli* (available from Sigma Aldrich).

Current multivalent conjugate vaccines are made by synthesis of individual conjugate vaccines first, followed by their mixing to produce a "cocktail" conjugate vaccine (e.g., the Wyeth hepta-valent pneumococcal vaccine, Prevnar®). The present invention's methods of making vaccines can be used to make multivalent vaccines by mixing chemically different antigens, e.g., capsular organic polymers, together before cross-linking the carrier protein, e.g., with glutaraldehyde, or by mixing specific vaccines of the invention that were synthesized separately. This flexibility provides significant advantages over the present methods of manufacturing multivalent vaccines.

Exemplary vaccines of the invention discussed in the examples, PCMV vaccines #1-3, performed like conjugate vaccine despite the fact that these vaccines were synthesized by a method that is not predicted to generate any covalent bonds between atoms making up the PGA molecule and DNI protein. Glutaraldehyde reacts exclusively with amino side chains of proteins typified by the epsilon amino group of lysine residues. The PGA polymer contains no free amino groups and possesses only carboxyl side-chains which do not react with glutaraldehyde. Thus, the conjugate-like immune responses generated by PCMVs indicate that long PGA molecules were molecularly entrapped within a cross-linked matrix of DNI protein molecules.

According to a non-limiting model, the entrapment acts to carry DNI protein and PGA into B-cells that bind such matrixes by virtue of Ig receptors that recognize PGA immunologically. Once taken up inside these B cells, the matrixes are degraded in a manner similar to conventional conjugate vaccines and that this results in DNI-derived peptides that are displayed on MHC-II molecules of the corresponding B-cells. This in turn recruits T-cell help and thus leads to the expansion and maturation of such B cells to become IgG producing plasma and memory cells specific for PGA. Thus, according to the non-limiting model PCMVs work like protein-conjugate capsular vaccines immunologically but are distinct because PCMVs lack significant covalent bonding between the carrier protein and the capsular polymers.

The vaccines of the invention, including PCMVs, may be used in combination, for example, in pediatric vaccines. In addition, the vaccines of the invention may be used to vaccinate against, for example, *Pneumococcus* infection, *Streptococcus* (groups A and B) infection, *Haemophilus influenzae* type B ("HiB") infection, meningococcal (e.g., *Neisseria meningitides*) infection, and may be used as O antigen vaccines from Gram negative bacteria (e.g., *Pseudomonas aeruginosa, Francisella tularensis* (Thirumalapura et al., J. Med. Microbiol. 54:693-695, 2005; Vinogradov and Perry, Carbohydr. Res. 339:1643-1648, 2004; Vinogradov et al., Carbohydr. Res. 214:289-297, 1991), *Shigella* species, *Salmonella* species, *Acinetobacter* species, *Burkholderia* species, and *Escherichia coli*).

Vaccines of the invention may be made using any linkers, such as, e.g., those described herein, to cross-link any carrier protein, such as, e.g., those described herein, in the presence of one or more antigens of interest, such as, e.g., those described herein. If one antigen of interest is used, the protein matrix vaccine of the invention is said to be monovalent. If more than one antigen of interest is used, the protein matrix vaccine of the invention is said to be multivalent. If a microbial capsular polymer is the antigen of interest, the protein matrix vaccine of the invention is said to be a protein capsular matrix vaccine (PCMV).

Linkers

Cross-linking carrier proteins are well known in the art and include glutaraldehyde, m-maleimidobenzoyl-N-hydroxysuccinimide ester, carbodiimide, and bis-biazotized benzidine.

General methods and moieties for directly cross-linking carrier proteins, using a homobifunctional or a heterobifunctional linkers are described, for example, by G. T. Hermanson in Bioconjugate Techniques, Academic Press, 1996 and Dick and Beurret in Conjugate Vaccines. Contribu. Microbiol. Immunol., Karger, Basal 10:48-114, 1989. For example, with a carrier protein possessing n number of lysine moieties, there are, theoretically, n+1 primary amines (including the terminal amine) available for reaction with an exemplary cross-linker's carboxylic group. Thus, using this direct conjugation procedure the product is limited to having n+1 amide bonds formed.

The linker employed in desirable embodiments of the present invention is, at its simplest, a bond connecting two carrier proteins. The linker can be, a linear, cyclic, or branched molecular skeleton, with pendant groups which bind covalently to two carrier proteins, (A) and (B). Any given carrier protein may be linked to more than one carrier protein, such that a matrix of interconnected carrier proteins is created, in which an antigen may be enclosed.

The term linkage group refers to the covalent bond that results from the combination of reactive moieties of linker (L) with functional groups of (A) or (B). Examples of linkage groups include, without limitation, ester, carbamate, thioester, imine, disulfide, amide, ether, thioether, sulfonamide, isourea, isothiourea, imidoester, amidine, phosphoramidate, phosphodiester, thioether, and hydrazone.

The linking of (A) with (B) is achieved by covalent means, involving bond (linkage group) formation with one or more functional groups located on (A) and (B). Examples of chemically reactive functional groups which may be employed for this purpose include, without limitation, amino, hydroxyl, sulfhydryl, carboxyl, carbonyl, thioethers, guanidinyl, imidazolyl, and phenolic groups, all of which are present in naturally-occurring amino acids in many carrier proteins.

The covalent linking of (A) with (B) may therefore be effected using a linker (L) which contains reactive moieties capable of reaction with such functional groups present in (A) and (B). The product of this reaction is a linkage group which contains the newly formed bonds linking (L) with (A) and (L) with (B). For example, a hydroxyl group of (A) may react with a carboxylic acid group of (L), or an activated derivative thereof, vide infra, resulting in the formation of an ester linkage group.

Examples of moieties capable of reaction with sulfhydryl groups include α-haloacetyl compounds of the type XCH$_2$CO— (where X=Br, Cl, or I), which show particular reactivity for sulfhydryl groups, but which can also be used to modify imidazolyl, thioether, phenol, and amino groups as described by, for example, Gurd, *Methods Enzymol.* 11:532, 1967. N-Maleimide derivatives are also considered selective towards sulfhydryl groups, but may additionally be useful in coupling to amino groups under certain conditions. Reagents such as 2-iminothiolane (Traut et al., *Biochemistry* 12:3266, 1973), which introduce a thiol group through conversion of an amino group, may be considered as sulfhydryl reagents if linking occurs through the formation of disulphide bridges.

Examples of reactive moieties capable of reaction with amino groups include, for example, alkylating and acylating agents. Representative alkylating agents include:

(i) α-haloacetyl compounds, which show specificity towards amino groups in the absence of reactive thiol groups and are of the type XCH$_2$CO— (where X=Cl, Br or I) as described by, for example, Wong (Biochemistry 24:5337, 1979);

(ii) N-maleimide derivatives, which may react with amino groups either through a Michael type reaction or through acylation by addition to the ring carbonyl group as described by, for example, Smyth et al. (J. Am. Chem. Soc. 82:4600, 1960 and *Biochem. J.* 91:589, 1964);

(iii) aryl halides such as reactive nitrohaloaromatic compounds;

(iv) alkyl halides, as described by, for example, McKenzie et al. (J. Protein Chem. 7:581, 1988);

(v) aldehydes and ketones capable of Schiff's base formation with amino groups, the adducts formed usually being stabilized through reduction to give a stable amine;

(vi) epoxide derivatives such as epichlorohydrin and bisoxiranes, which may react with amino, sulfhydryl, or phenolic hydroxyl groups;

(vii) chlorine-containing derivatives of s-triazines, which are very reactive towards nucleophiles such as amino, sufhydryl, and hydroxyl groups;

(viii) aziridines based on s-triazine compounds detailed above as described by, for example, Ross (J. Adv. Cancer Res. 2:1, 1954), which react with nucleophiles such as amino groups by ring opening;

(ix) squaric acid diethyl esters as described by, for example, Tietze (Chem. Ber. 124:1215, 1991); and (x) α-haloalkyl ethers, which are more reactive alkylating agents than normal alkyl halides because of the activation caused by the ether oxygen atom, as described by, for example, Benneche et al. (Eur. J. Med. Chem. 28:463, 1993).

Representative amino-reactive acylating agents include:

(i) isocyanates and isothiocyanates, particularly aromatic derivatives, which form stable urea and thiourea derivatives respectively;

(ii) sulfonyl chlorides, which have been described by, for example, Herzig et al. (Biopolymers 2:349, 1964);

(iii) acid halides;

(iv) active esters such as nitrophenylesters or N-hydroxysuccinimidyl esters;

(v) acid anhydrides such as mixed, symmetrical, or N-carboxyanhydrides;

(vi) other useful reagents for amide bond formation as described by, for example, M. Bodansky (Principles of Peptide Synthesis, Springer-Verlag, 1984);

(vii) acylazides, e.g., where the azide group is generated from a preformed hydrazide derivative using sodium nitrite, as described by, for example, Wetz et al. (Anal. Biochem. 58:347, 1974); and (viii) imidoesters, which form stable amidines on reaction with amino groups as described by, for example, Hunter and Ludwig (J. Am. Chem. Soc. 84:3491, 1962).

Aldehydes, such as, e.g., glutaraldehyde, and ketones may be reacted with amines to form Schiff's bases, which may advantageously be stabilized through reductive amination. Alkoxylamino moieties readily react with ketones and aldehydes to produce stable alkoxamines as described by, for example, Webb et al. (Bioconjugate Chem. 1:96, 1990).

Examples of reactive moieties capable of reaction with carboxyl groups include diazo compounds such as diazoacetate esters and diazoacetamides, which react with high specificity to generate ester groups as described by, for example, Herriot (Adv. Protein Chem. 3:169, 1947). Carboxylic acid modifying reagents such as carbodiimides, which react through O-acylurea formation followed by amide bond formation, may also be employed.

The functional groups in (A) and/or (B) may, if desired, be converted to other functional groups prior to reaction, for example, to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane, or thiol-containing succinimidyl derivatives; conversion of thiols to carboxylic acids using reagents such as α-haloacetates; conversion of thiols to amines using reagents such as ethylenimine or 2-bromoethylamine; conversion of carboxylic acids to amines using reagents such as carbodiimides followed by diamines; and conversion of alcohols to thiols using reagents such as tosyl chloride followed by transesterification with thioacetate and hydrolysis to the thiol with sodium acetate.

So-called zero-length linkers, involving direct covalent joining of a reactive chemical group of (A) with a reactive chemical group of (B) without introducing additional linking material may, if desired, be used in accordance with the invention. Examples include compounds in which (L) represents a chemical bond linking an oxygen atom of (A) to a carbonyl or thiocarbonyl moiety present in (B), such that the linkage group is an ester or thioester. For example, an amino group (A) can be linked to a carboxyl group (B) by using carbodiimide chemistry yielding A-L-B where L is a amide bond or R—C=O linked to N—R where R is the carbon chain derived from amino acid side chains of the same or two different protein molecules.

Most commonly, however, the linker includes two or more reactive moieties, as described above, connected by a spacer element. The presence of a spacer permits bifunctional linkers to react with specific functional groups within (A) and (B), resulting in a covalent linkage between these two compounds. The reactive moieties in a linker (L) may be the same (homobifunctional linker) or different (heterobifunctional linker, or, where several dissimilar reactive moieties are present, heteromultifunctional linker), providing a diversity of potential reagents that may bring about covalent attachment between (A) and (B).

Spacer elements typically consist of chains which effectively separate (A) and (B) by a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, or —$(CH_2CH_2O)_nCH_2CH_2$—, in which n is 1 to 4.

The nature of extrinsic material introduced by the linking agent may have a bearing on the pharmacokinetics and/or activity of the ultimate vaccine product. Thus it may be desirable to introduce cleavable linkers, containing spacer arms which are biodegradable or chemically sensitive or which incorporate enzymatic cleavage sites.

These cleavable linkers, as described, for example, in PCT Publication WO 92/17436 (hereby incorporated by reference), are readily biodegraded in vivo. In some cases, linkage groups are cleaved in the presence of esterases, but are stable in the absence of such enzymes. (A) and (B) may, therefore, advantageously be linked to permit their slow release by enzymes active near the site of disease.

Linkers may form linkage groups with biodegradable diester, diamide, or dicarbamate groups of formula I:

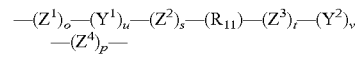

$$-(Z^4)_p-$$ I where, each of $Z^1$, $Z^2$, $Z^3$, and $Z^4$ is independently selected from O, S, and $NR_{12}$ (where $R_{12}$ is hydrogen or an alkyl group); each of $Y^1$ and $Y^2$ is independently selected from a carbonyl, thiocarbonyl, sulphonyl, phosphoryl or similar acid-forming group; o, p, s, t, u, and v are each independently 0 or 1; and $R_{11}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_qCH_2CH_2$— in which q is 1 to 4, or a chemical bond linking —$(Z^1)_o$—$(Y^1)_u$—$(Z^2)_s$— to —$(Z^3)_t$—$(Y^2)_v$—$(Z^4)_p$—.

Exemplary desirable linkers (L) used in the present invention may be described by any of formulas II-III:

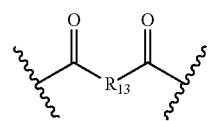

II

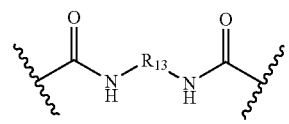

III where the linker is covalently attached to both an oxygen atom (A) and an oxygen atom of (B). Accordingly, linker (L) of formulas II-III are attached to carrier proteins (A) and (B) via dipyran, ester, or carbamate linkage groups. In these embodiments, $R_{13}$ represents a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$— in which n is 1 to 4, or a chemical bond linking two nitrogens or two carbonyls.

Linkers designed to form hydrazone linkages have the chemical formula IV:

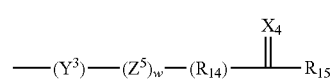

IV where $Z^5$ is selected from O, S, or $NR_{16}$; $R_{16}$ is hydrogen or an alkyl group; $R_{15}$ is selected from hydrogen, an alkyl, or a heteroalkyl; $Y^3$ is selected from a carbonyl, thiocarbonyl, sulphonyl, phosphoryl, or a similar acid-forming group covalently bound to an oxygen atom of (A); w is 0 or 1; $R_{14}$ is a linear or branched alkyl of 1 to 10 carbon atoms, a linear or branched heteroalkyl of 1 to 10 atoms, a linear or branched alkene of 2 to 10 carbon atoms, a linear or branched alkyne of 2 to 10 carbon atoms, an aromatic residue of 5 to 10 carbon atoms, a cyclic system of 3 to 10 atoms, —$(CH_2CH_2O)_nCH_2CH_2$—, in which n is 1 to 4, or a chemical bond linking —$(Y^3)$—$(Z^5)_w$— to

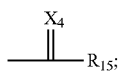

and $X_4$ is a hydrazone resulting from the condensation reaction of (B) containing a hydrazide group and the precursor to linker II, in which $X_4$ is the oxygen atom of a ketone or aldehyde group.

Carrier Proteins

In general, any carrier protein that can be entrapped with an antigen under physiological conditions may be used in the present invention. Desirably, the antigen is entrapped in a complex with carrier proteins in the absence of significant covalent bonding between the antigen and a carrier protein. Absence of significant covalent bonding, refers to no more than 50% of the antigen being covalently bonded to a carrier protein. In desirable embodiments, no more than 40%, 30%, 10%, or 5% of the antigen is covalently bonded to a carrier protein. The antigen/carrier protein complex may contain another compound, such as alum, and this other compound, in desirable embodiments, can entrap the antigen and carrier protein.

Carrier proteins used in the vaccines of the invention desirably are proteins that, either alone or in combination with an antigen, invoke an immune response in a subject. Desirably, the carrier protein contains at least one epitope recognized by a T-cell. Desirably, the epitope is capable of inducing a T-cell response in a subject, and induce B-cells to produce antibodies against the entire antigen of interest. Epitopes as used in describing this invention, include any determinant on an antigen that is responsible for its specific interaction with an antibody molecule or fragment thereof. Epitopic determinants usually consist of chemically active surface groupings of molecules such as amino acids or sugar side chains and have specific three-dimensional structural characteristics as well as specific charge characteristics. To have immunogenic properties, a protein or polypeptide generally is capable of stimulating T-cells. However, a carrier protein that lacks an epitope recognized by a T-cell may also be immunogenic.

By selecting a carrier protein which is known to elicit a strong immunogenic response, a diverse population of subjects can be treated by a PCMV described herein. The carrier protein desirably is sufficiently foreign to elicit a strong immune response to the vaccine. Typically, the carrier protein used is a molecule that is capable of imparting immunogenicity to the antigen of interest. In a desirable embodiment, a carrier protein is one that is inherently highly immunogenic. Thus a carrier protein that has a high degree of immunogenicity and is able to maximize antibody production to the antigens complexed with it is desirable.

Various carrier proteins of the invention include, e.g., toxins and toxoids (chemical or genetic), which may or may not be mutant, such as anthrax toxin, PA and DNI (PharmAthene, Inc.), diphtheria toxoid (Massachusetts State Biological Labs; Serum Institute of India, Ltd.) or CRM 197, tetanus toxin, tetanus toxoid (Massachusetts State Biological Labs; Serum Institute of India, Ltd.), tetanus toxin fragment Z, exotoxin A or mutants of exotoxin A of *Pseudomonas aeruginosa*, bacterial flagellin, pneumolysin, an outer membrane protein of *Neisseria meningitidis* (strain available from the ATCC (American Type Culture Collection, Manassas, Va.)), *Pseudomonas aeruginosa* Hcp1 protein, *Escherichia coli* heat labile enterotoxin, shiga-like toxin, human LTB protein, a protein extract from whole bacterial cells, and any other protein that can be cross-linked by a linker.

Desirably, the carrier protein is the cholera toxin B subunit (available from SBL Vaccin AB), diphtheria toxin (Connaught, Inc.), tetanus toxin Fragment C (available from Sigma Aldrich), DNI, or beta-galactosidase from *Escherichia coli* (available from Sigma Aldrich). Other desirable carrier proteins include bovine serum albumin (BSA), P40, and chicken riboflavin. (Unless otherwise indicated, the exemplary carrier proteins are commercially available from Sigma Aldrich.) Other exemplary carrier proteins are MAPs (multi-antigenic peptides), which are branched peptides. By using a MAP, cross-linking density is maximized because of multiple branched amino acid residues. An exemplary amino acid that can be used to form a MAP is, but is not limited to, lysine.

Both BSA and keyhole limpet hemocyanin (KLH) have commonly been used as carriers in the development of vaccines when experimenting with animals. Carrier proteins which have been used in the preparation of therapeutic vaccines include, but are not limited to, a number of toxins of pathogenic bacteria and their toxoids. Examples include diphtheria and tetanus toxins and their medically acceptable corresponding toxoids. Other candidates are proteins antigenically similar to bacterial toxins referred to as cross-reacting materials (CRMs). Carrier proteins of the invention may also include any protein not derived from humans and not present in any human food substance.

In desirable embodiments of the invention, proteins that form ring-like structures are used for PCMV production. Such proteins include the Hcp1 protein of *Pseudomonas aeruginosa*, the nontoxic "B subunits" of cholera toxin, the heat-labile enterotoxin of *Escherichia coli*, and shiga-like toxin. Such ring-like protein complexes can form "beads on a string" where the linear PS chains penetrate the central channel of these ring-shaped protein complexes. After protein cross-linking, such complexes are predicted to be particularly stable. Structural data of the proteins suggest these central channels are large enough for PS chains to enter easily. For example, the central channel of the Hcp1 hexameric ring is 42 Angstoms which is wide enough to easily accommodate several polysaccharide chains of 5.5 Angstoms in width (Mougous et al., Science 312(5779):1526-1530, 2006). Alternatively, protein rings may be assembled around the PS (e.g., from subunits of a monomeric carrier protein that naturally assemble into rings under particular physical chemical conditions). Such monomeric proteins that can assemble into rings are known in the art and include, for example, pneumolysin (Walker et al., Infect. Immun. 55(5):1184-1189, 1987; Kanclerski and Mollby, J. Clin. Microbiol. 25(2):222-225, 1987), listeriolysin O (Kayal and Charbit, FEMS Microbiol. Rev. 30:514-529, 2006; Mengaud et al., Infect. Immun. 55(12):3225-3227, 1987), DNI, anthrax PA, Hcp1, cholera toxin B subunit, shiga toxin B subunit, Flagellin, and numerous related molecules known in the art and made by various microorganisms.

In another desirable embodiment, Toll-like receptor (TLR) agonists are used as carrier proteins. Toll-like receptor (TLR) activation is important in shaping the adaptive immune response and may play a role in affinity maturation of the antibody response, isotype switching, and immunological memory. Flagellin (FLA) of *Vibrio cholerae* is a TLR agonist. Over 20 mgs of FLA protein has been purified from recombinant *Escherichia coli* and shown to be a potent TLR activator in the IL-6 macrophage induction assay described herein. In addition, a well-conserved *Streptococcus pneumoniae* protein called "Pneumolysin" has also been shown to activate TLR4 and, additionally, is a protective antigen. Thus, this protein can also be used as a PCMV carrier protein.

Further, outer membrane protein (OMP) mixtures (e.g., the OMPs of *Neisseria meningitidis*) are used as the carrier protein for HIB conjugate vaccine produce by Merck and protein extracts from whole *Streptococcal pneumoniae* bacterial cells have been shown to be at least partially protective in animal infection model. In desirable embodiments of the invention, these protein mixtures are the source of PCMV carrier protein.

In a desirable embodiment, the PCMV method is used with a carrier protein that has, e.g., at least 2 lysine residues or other residues that are unblocked and that can be cross-linked by chemical modification. In other desirable embodiments, the carrier protein is a multimer (e.g., one containing at least 5 subunits). Desirably, the multimer is a homomultimer.

In another embodiment, DNI is used as the carrier protein because it is nontoxic leaving no need to detoxify the protein before use. Furthermore, the use of DNI is desirable because DNI may also induce a protective immune response to *B. anthracis*, in addition to the protective immune response to the antigen of interest. Also, DNI has no internal disulfide bonds. Such bonds are susceptible to borohydride reduction, which could denature the protein and result in loss of epitopes that induce anthrax toxin neutralizing antibody.

Antigens of Interest

The vaccine compositions of the invention and methods of making and administering such vaccines can be used for any antigen of interest, e.g., a polysaccharide, polyalcohol, or poly amino acid. Desirably, the antigen of interest carries no primary groups that can be destroyed by the chemical reactions employed by the method of making vaccines, e.g., the denaturing of an antigen caused by the destruction of antigen disulfide bonds by borohydride reduction. Exemplary antigens of interest include organic polymers such as polysaccharides (e.g., polysaccharides having at least 18 residues), phosphopolysaccharides, polysaccharides with amino sugars with N-acetyl substitutions, polysaccharides containing sulfanylated sugars, other sulfate-modified sugars, or phosphate-modified sugars, polyalcohols, poly amino acids, teichoic acids, O side chains of lipopolysaccharides. Exemplary antigens of interest also include capsular organic polymers including those synthesized by microbes, e.g., bacteria, fungi, parasites, and viruses, and then purified from such a biological source using standard methods. Exemplary antigens of interest include microbial capsular organic polymers including those purified from bacterial organisms such as *Bacillus* species (including *B. anthracis*) (Wang and Lucas, Infect. Immun. 72(9):5460-5463, 2004), *Streptococcus pneumoniae* (Bentley et al., PLoS Genet. 2(3):e31, Epub 2006; Kolkman et al., J. Biochemistry 123:937-945, 1998; and Kong et al., J. Med. Micorbiol. 54:351-356, 2005), *Shigella* (Zhao et al., Carbohydr. Res. 342(9):1275-1279, Epub 2007), *Haemophilus influenzae, Neisseria meningitidis, Staphylococcus aureus, Salmonella typhi, Streptococcus pyogenes, Escherichia coli* (Zhao et al., Carbohydr. Res. 342(9):1275-1279, Epub 2007), and *Pseudomonas aeruginosa*, and fungal organisms such as Cryptococcus and Candida, as well as many other microorganisms (see, e.g., Ovodov, Biochemistry (Mosc.) 71(9):937-954, 2006; Lee et al., Adv. Exp. Med. Biol. 491:453-471, 2001; and Lee, Mol. Immunol. 24(10):1005-1019, 1987). Exemplary antigens of interest also include polymers that do not occur in nature and thus are non-biological in origin.

Vaccine Compositions

The vaccines of the invention, including PCMVs, may be used in combination, for example, in pediatric vaccines. In addition, the vaccines of the invention may be used to vaccinate against, for example, *Pneumococcus infection, Haemophilus influenzae* type B ("HiB") infection, *Streptococcus* (groups A and B) infection, meningococcal (e.g., *Neisseria meningitides*) infection, and may be used as O antigen vaccines from Gram negative bacteria (e.g., *Pseudomonas aeruginosa, Francisella tularensis, Shigella* species, *Salmonella* species, *Acinetobacter* species, *Burkholderia* species, and *Escherichia coli*).

The vaccine formulation desirably includes at least one carrier protein, one or more antigen of interest, and a pharmaceutically acceptable carrier or excipient (e.g., aluminum phosphate, sodium chloride, and sterile water). A vaccine composition may also include an adjuvant system for enhancing the immunogenicity of the formulation, such as oil in a water system and other systems known in the art or other pharmaceutically acceptable excipients. A carrier/antigen complex that is insoluble under physiological conditions is desirable to slowly release the antigen after administration to a subject. Such a complex desirably is delivered in a suspension containing pharmaceutically acceptable excipients. However, the carrier/antigen complex may also be soluble under physiological conditions.

Typically the vaccine is in a volume of about 0.5 mL for subcutaneous injection, 0.1 mL for intradermal injection, or 0.002-0.02 mL for percutaneous administration. A 0.5 ml dose of the vaccine may contain approximately 2-500 μg of the antigen entrapped with approximately 2-500 μg of the carrier protein. In a desirable embodiment, in a 0.5 ml dose, approximately 10 μg of the antigen are entrapped with approximately 10 μg of the carrier protein. The molar ratio of antigen to carrier protein desirably is between 1 to 10 (e.g., 1 part antigen to 2 parts carrier or 1 part antigen to 3 parts carrier) and 10 to 1 (e.g., 3 parts antigen to one part carrier or 2 parts antigen to 1 part carrier). In a desirable embodiment, the molar ratio of antigen to carrier is 1 to 1. Alternatively, the ratio by dry weight of antigen to carrier protein desirably is between 1 to 10 and 10 to 1 (e.g., 1 to 1 by dry weight).

Because the peptides or conjugates may be degraded in the stomach, the vaccine is desirably administered parenterally (for instance, by subcutaneous, intramuscular, intravenous, or intradermal injection). While delivery by a means that physically penetrates the dermal layer is desirable (e.g., a needle, airgun, or abrasion), the vaccines of the invention can also be administered by transdermal absorption.

In particular, the vaccines of the invention may be administered to a subject, e.g., by intramuscular injection, intradermal injection, or transcutaneous immunization with appropriate immune adjuvants. Vaccines of the invention may be administered, one or more times, often including a second administration designed to boost production of antibodies in a subject to prevent infection by an infectious agent. The frequency and quantity of vaccine dosage depends on the specific activity of the vaccine and can be readily determined by routine experimentation.

For example, for an infant, a vaccine schedule may be three doses of 0.5 ml each at approximately four to eight week intervals (starting at two-months of age) followed by a fourth dose of 0.5 ml at approximately twelve to fifteen months of age. A fifth dose between four and six years of age may be desirable for some vaccines.

While the age at which the first dosage is administered generally is two-months, a vaccine may be administered to infants as young as 6 weeks of age. For children who are beyond the age of a routine infant vaccination schedule, the vaccines of the invention may be administered according to the following exemplary schedule.

| Age of first dosage | Dosage schedule |
|---|---|
| 7-11 months of age | Total of three 0.5 ml doses; the first two at least four weeks apart and the third at least two months after the second dose |
| 12-23 months of age | Total of two 0.5 ml doses at least two months apart |
| 24 months to 9 years of age | One 0.5 ml dose |

For adults, two or more 0.5 ml doses given at internals of 2-8 week in between generally are sufficient to provide long-term protection. A booster dose is desirably given every ten years to previously immunized adults and children above eleven years of age.

The formulations may be presented in unit-dose or multi-dose containers, for example, sealed ampoules and vials and may be stored in a freeze-dried (lyophilized) condition requiring only the addition of the sterile liquid carrier immediately prior to use. Vaccines of the invention can be formulated in pharmacologically acceptable vehicles, e.g., alum hydroxide gel, adjuvant preparation, or saline, and then administered, e.g., by intramuscular injection, intradermal injection, or transcutaneous immunization with appropriate immune adjuvants.

The invention also includes kits that include a vaccine described herein (e.g., a PCMV). The kits of the invention can also include instructions for using the kits in the vaccination methods described herein.

The efficacy of the immunization schedule may be determined by using standard methods for measuring the antibody titer in the subject. In general, mean antibody titers (desirably IgG titers) of approximately 1 µg/ml are considered indicative of long-term protection.

The antigen/carrier protein complexes for use in the vaccine compositions described herein are desirably between 10 nm and 100 µm in diameter. Viruses can be 100 nm in diameter and are immunogenic. Whole bacteria are 1-10 µm in diameter and are also immunogenic. A small clump of bacteria can be about 100 µm in diameter. In particular embodiments, an antigen/carrier protein complex in a vaccine composition desirably is between 100 nm and 10 µm in diameter. This complex may be soluble or insoluble.

The invention is described herein below by reference to specific examples, embodiments and figures, the purpose of which is to illustrate the invention rather than to limit its scope. The following examples are not to be construed as limiting.

EXAMPLES

Example 1

Vaccine and Control Preparations

Capsular poly gamma-D-glutamic acid (PGA) was purchased from Vedan (Taiwan) or purified by the method of Rhie et al. (Proc. Natl. Acad. Sci. USA 100:10925-10930, 2003). Dominant negative mutant (DNI) is a mutated form of protective antigen (PA) of *B. anthracis* and was produced from *Escherichia coli* by the method of Benson, et al. (Biochemistry 37:3941-3948, 1998). PGA and DNI protein were exhaustively dialyzed against 0.05M sodium phosphate buffer pH 7.4 (SP7.4) before use. The DNI stock solution contained 30 mg/ml. The PGA stock solution contained 134 mg/ml. The linker glutaraldehyde was purchased from Pierce as a 25% stock solution. Protein Capsular Matrix Vaccines (PCMVs) and controls were assembled in reactions according to the Table 1.

TABLE 1

Assembly of reactions for production of PCMV preparations 1-3 and controls 4 and 5

| Reaction # | DNI ml | PGA ml | dH2O ml | 25% glutaraldehyde ml | Name |
|---|---|---|---|---|---|
| 1 | 20 | 1 | 3 | 0.8 | PCMV1 |
| 2 | 12 | 4 | 8 | 0.8 | PCMV2 |
| 3 | 16 | 2 | 6 | 0.8 | PCMV3 |
| 4 | 16 | 2 | 6 | 0 | P + C control |
| 5 | 16 | 0 | 8 | 0.8 | P only control |

The five reactions were assembled at room temperature (22° C.) without glutaraldehyde. At T=0, 0.1 ml of 25% glutaraldehyde (G25) was added to the indicated reactions. Each 30 seconds thereafter another 0.1 ml of G25 was added and this was repeated until each indicated reaction had received 0.8 ml of G25 in total. The cross-linking of DNI molecules by the bi-functional glutaraldehyde molecules could be observed macroscopically by the generation of varying degrees of turbidity and insoluble "gel" like particles in the following order: most turbidity and gel formation, reactions 1>2>3>4, with reaction 5 remaining totally clear and soluble. After 1 hour, 2 ml of 1 M sodium borohydride in 0.5 M sodium borate buffer pH 9.3 (SBH) was added to all six reactions to reduce Schiff bases formed between the amino side chains of the DNI molecules and the bi-functional glutaraldehyde molecules. Silicone antifoam (0.01 ml) was added to each reaction to control foaming during this reaction. The reactions were stored at 4° C. for 72 hours. All reactions were then dialyzed exhaustively against SP7.4, for 48 hours. Insoluble material was removed by centrifugation of the final products and stored at 4° C. until use.

A conventional conjugate between bovine serum albumin (BSA) and PGA was synthesized by coupling the amino groups of BSA to the carboxyl groups of PGA using the water soluble carbodiimide, EDAC (1-ethly-3-(3-dimethyl-aminopropyl)carbodiimide), as follows: 5 ml of 30 mg/ml BSA in water was mixed with 1 ml of 134 mg/ml PGA in NP7.5. 50 mg of EDAC was added and the reaction was allowed to proceed at RT for 3 hours. The reaction was dialyzed at 4° C. for 18 hours against SP7.4 containing 1 mM glycine to block activated groups and then at 4° C. for 24 hours against SP7.4 only. The final product is referred to as PGA-BSA conjugate.

After synthesis and dialysis of PCMV and control preparations the molecular state of the DNI protein was examined to confirm that glutaraldehyde had indeed molecularly cross-linked the protein in the presence or absence of various amounts of PGA. PCMV and control preparations were monitored for such cross-linking by SDS (sodium dodecyl sulphate) polyacryamide gel electrophoresis and Western blotting with anti-PA antiserum. As shown in FIG. 2, DNI protein migrates at 84 kDa before glutaraldehyde cross-linking. PCVM1-PCMV3 (lanes 1-3) show extensive cross-linking of the DNI protein as evidenced by the migration of bands at molecular masses greater than 220 kDa. DNI protein alone cross-linked in the absence of PGA also shows the same high molecular weight species (lane 5). In contrast, DNI mixed with PGA but not treated with glutaraldehyde shows bands that co-migrate with DNI or lower molecular weight species (lane 4). Thus, the PGA preparation from Vedan (Taiwan) appeared to be contaminated with a protease active against DNI. Samples of Vedan PGA run in lane 6 however did not show high levels of contaminating proteins that react with the anti-PA antiserum, suggesting that the observed bands were DNI-derived products of the various reactions.

In addition, PGA and one or more of the pneumococcal PS as antigens is used to explore whether FLA (flagellin of *Vibrio cholerae*) is a better carrier protein than DNI in the context of PCMVs. The effect of the carrier protein is assessed by measuring the level of IgG directed against PGA, and PSs achieved by immunization with these various PCMVs as well as their potency on a weight of protein basis.

PCMVs can also be made by a procedure that cross-links amino groups to carboxy groups directly without the use of a bifunctional cross-linker. In particular, PCMVs can be made by cross-linking amino and carboxyl groups of the carrier proteins using carbodiimide chemistry. This chemistry forms peptide bonds between primary amino groups of lysine side chains and the carboxyl groups of aspartate and glutamate side chains. While amino groups are mostly blocked on formalin treated toxoids, formalin does not react with carboxyl groups at all. Thus, carbodiimide chemistry can be useful in making PCMVs using formalin toxoids that can resist glutaraldehyde cross-linking. Cross-linking is readily detected by SDS-PAGE. The presence of high molecular weight protein "smears" that depend on addition of a cross-linker like glutaraldehyde is indicative of cross-linking.

TABLE 2

Cross-linking of carrier proteins determined by SDS-PAGE analysis.

| Glutaraldehyde | No | Yes | Yes | Yes | Yes |
|---|---|---|---|---|---|
| Capsular Polymer | −PGA | −PGA | +PGA | +PS 6B | +PS 23F |
| BSA | − | + | + | + | + |
| Diphtheria Toxin | − | + | + | n.d. | n.d. |
| Diphtheria Toxoid | − | − | − | n.d. | n.d. |
| Tetanus Toxoid | − | + | + | n.d. | n.d. |

+ signs indicate cross-linking was detected by SDS-PAGE, − signs indicate protein migration was unaltered from that seen in the no glutaraldehtde control. n.d.—not determined (assay not performed).

For the experiments shown in Table 2, 200 microliter reactions were done in 50 mM HEPES pH 7.5 and incubated at ambient temperature for 2 hours. The reactions were quenched with 120 mM sodium borohydride. Glutaraldehyde was added to 64 mM, bovine serum albumin (BSA) was used at 15 mg/ml, diphtheria toxin, diphtheria toxoid, and tetanus toxoid were used at about 5 mg/ml, PGA was added at 13.4 mg/ml, pneumo PS type 6B and 23F were added at 4 mg/ml.

As shown in Table 2, some formalin treated proteins (e.g., diphtheria toxoid) do not cross-link well with glutaraldehyde and, therefore, require other cross-linking chemistry for use in PCMV preparation. Others, like tetanus toxoid, can be glutaraldehyde cross-linked but not to the same extent as unmodified proteins such as diphtheria toxin and bovine serum albumin.

Example 2

Immunization and Analysis of anti-DNI and Anti-PGA Immune Responses

The soluble products of the 5 reactions described in Table 1 were adjusted to the same protein concentration based on their absorbance at 280 nm. Approximately 5-7 week old BALB/c mice from Charles River were used in all immunization studies described in FIG. 2. Mice were immunized with PCMV vaccines 1-3 and antigen preparation controls 4 and 5 at a dose of 20 µg of DNI protein by intraperitoneal injection on day 0. All mice were bled on day 7 and then boosted with the same size doses of antigen preparations on day 10. The mice were bled again on day 17 and then boosted again on day 20. Mice were bled again on day 30 at which time they were sacrificed. Serum from blood samples was collected after clotting occurred and stored at −20° C. Enzyme-linked immunosorbent assay (ELISA) was used to assay for the level of anti-PGA and anti-DNI serum antibodies. In brief, Immulon 2HB ELISA (VWR) microtiter dishes were coated with either BSA-PGA or DNI in 0.1 M sodium carbonate buffer, pH 9.6 at 0.5 µg/well in a volume of 100 µl/well. After overnight incubation at 4° C., antigen-coated plates were blocked by incubation with 3% BSA (w/v) in TBS-0.1% Tween (TBST) for 1 hour at room temperature or overnight at 4° C. Serum samples pooled from groups of four mice from each time point post-boost were serially diluted in TBST and added to antigen-coated plates and incubated for at least 1 hour. Anti-DNI and anti-PGA antibody responses were determined using rabbit anti-serum against mouse IgG or IgM conjugated to alkaline phosphatase (Zymed). The substrate p-nitrophenyl phosphate (PNPP) was added to each well and the absorbance at 405 nm was determined spectrophotometrically for each reaction. Data are reported as the reciprocal endpoint titer, defined as the maximum dilution to obtain an $OD_{405}$ reading that is two standard deviations above that of the negative control.

Figure 3:
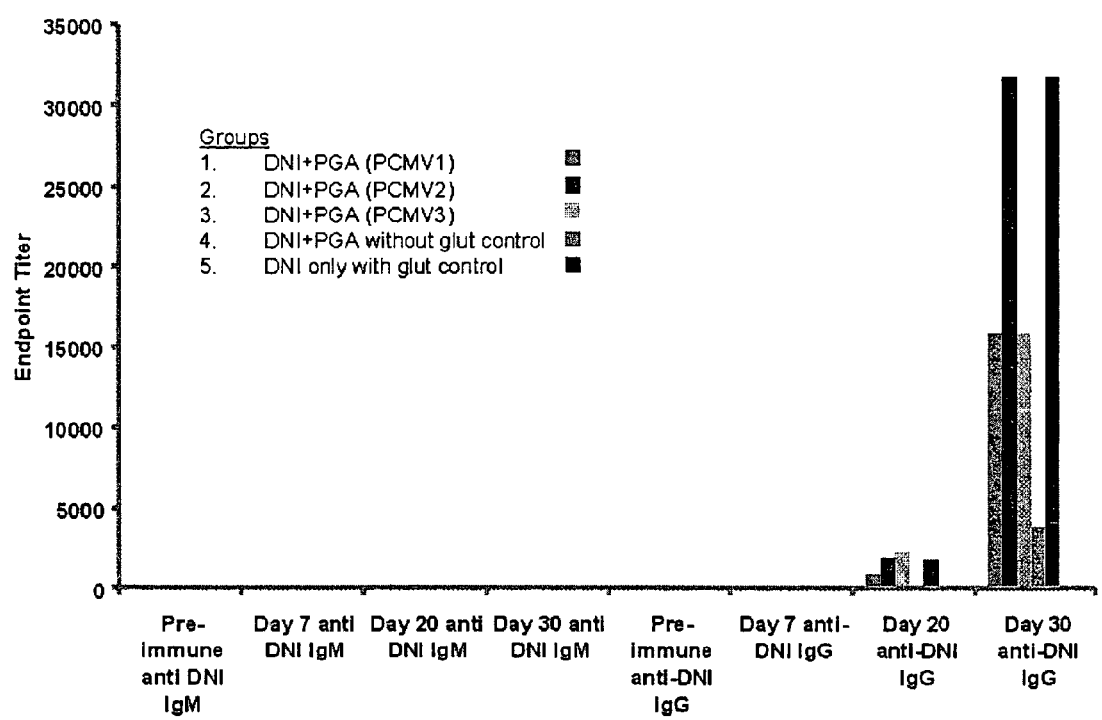
FIG. 3 is a graph showing the results of ELISA assays used to measure the IgM and IgG specific anti-DNI immune responses in mice immunized with three PCMV preparations (PCMV1-PCMV3; preparations 1-3) and the two antigen control preparations 4 and 5. The DNI protein was highly immunogenic in all preparations except control preparation 4 which was not cross-linked with glutaraldehyde (glut). However, these DNI-specific immune responses were exclusively IgG-based. While no anti-DNI IgM was detected even at day 7 of the immunization, a significant anti-DNI IgG response could be detected in mice immunized with PCMV preparations by day 17 and those immunized with cross-linked DNI only (preparation 5). A strong booster response was noted against DNI on day 30 with all preparations including preparation 4
Figure 4:
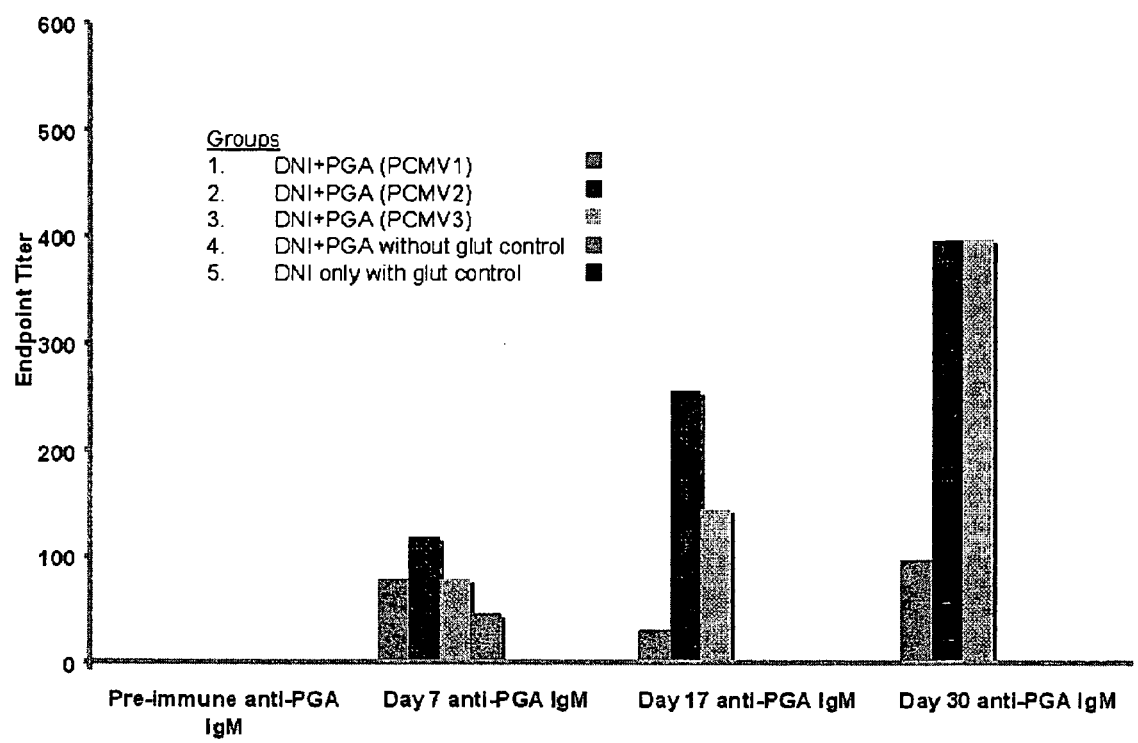
FIG. 4 is a graph showing the results of ELISA assays used to measure the IgM specific anti-PGA immune responses in mice immunized with the three PCMV preparations (PCMV1-PCMV3; preparations 1-3) and the two antigen control preparations 4 and 5. Anti-PGA IgM responses showed a pattern that was typical of a capsular polymer. The control preparation 4 generated a detectable anti-PGA IgM response on day 7 but this response was not boosted on day 17 or day 30. All PCMV preparations induced an anti-PGA IgM response on day 7 and then exclusively generated even stronger anti-PGA IgM responses on days 17 and 30. As expected the control preparation 5 (cross-linked DNI only) did not generate either an IgM- or IgG-based anti-PGA response
Figure 5:
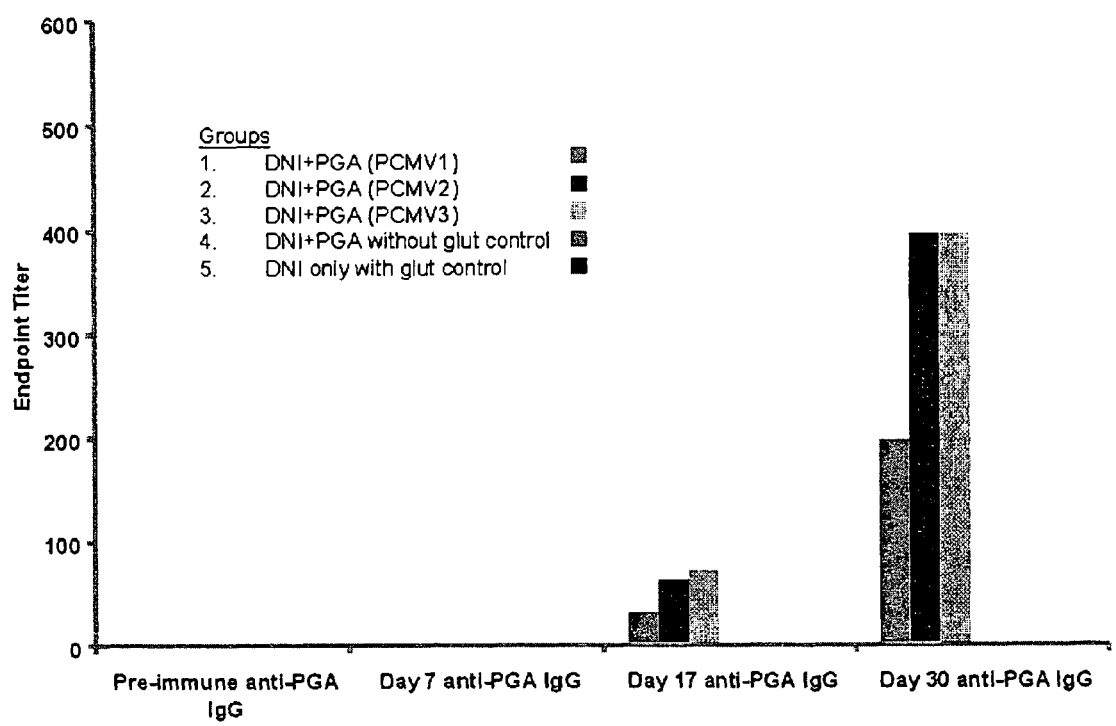
FIG. 5 is a graph showing the results of an ELISA assays used to measure the IgG specific anti-PGA immune response in mice immunized with the three PCMV preparations (PCMV1-PCMV3; preparations 1-3) and the two antigen control preparations 4 and 5. PCMV 1-3 generated strong IgG-based anti-PGA responses that were apparent on day 17 and then clearly boosted on day 30.
Figure 6:
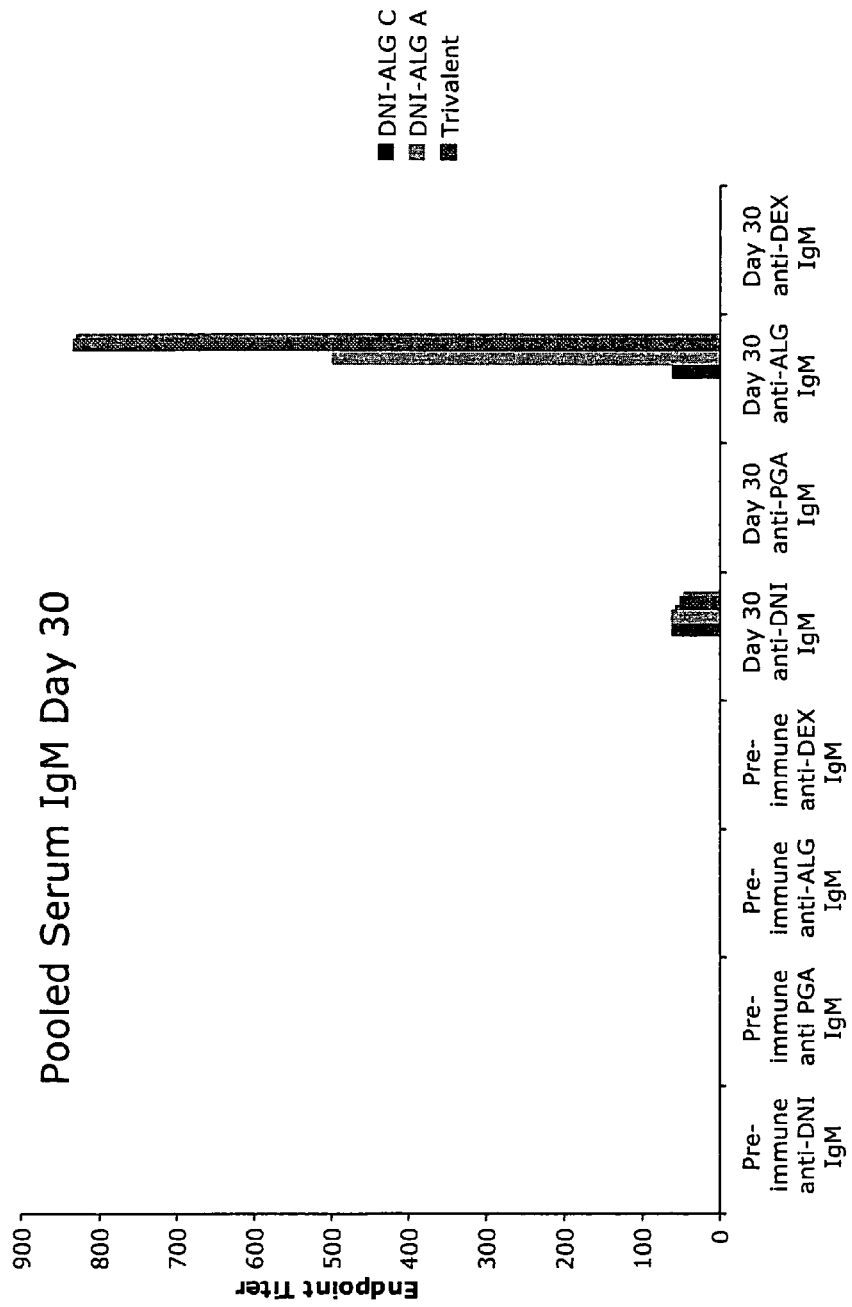
FIG. 6 is a graph showing the pooled serum IgM antibody titer pre-immunization and 30 days after immunization with PCMVs containing DNI and alginate (DNI-ALG C, DNI ALG A) and a "one pot" trivalent PCMV preparation containing DNI complexed with algenate (ALG), dextran (DEX), and PGA.
Figure 7:
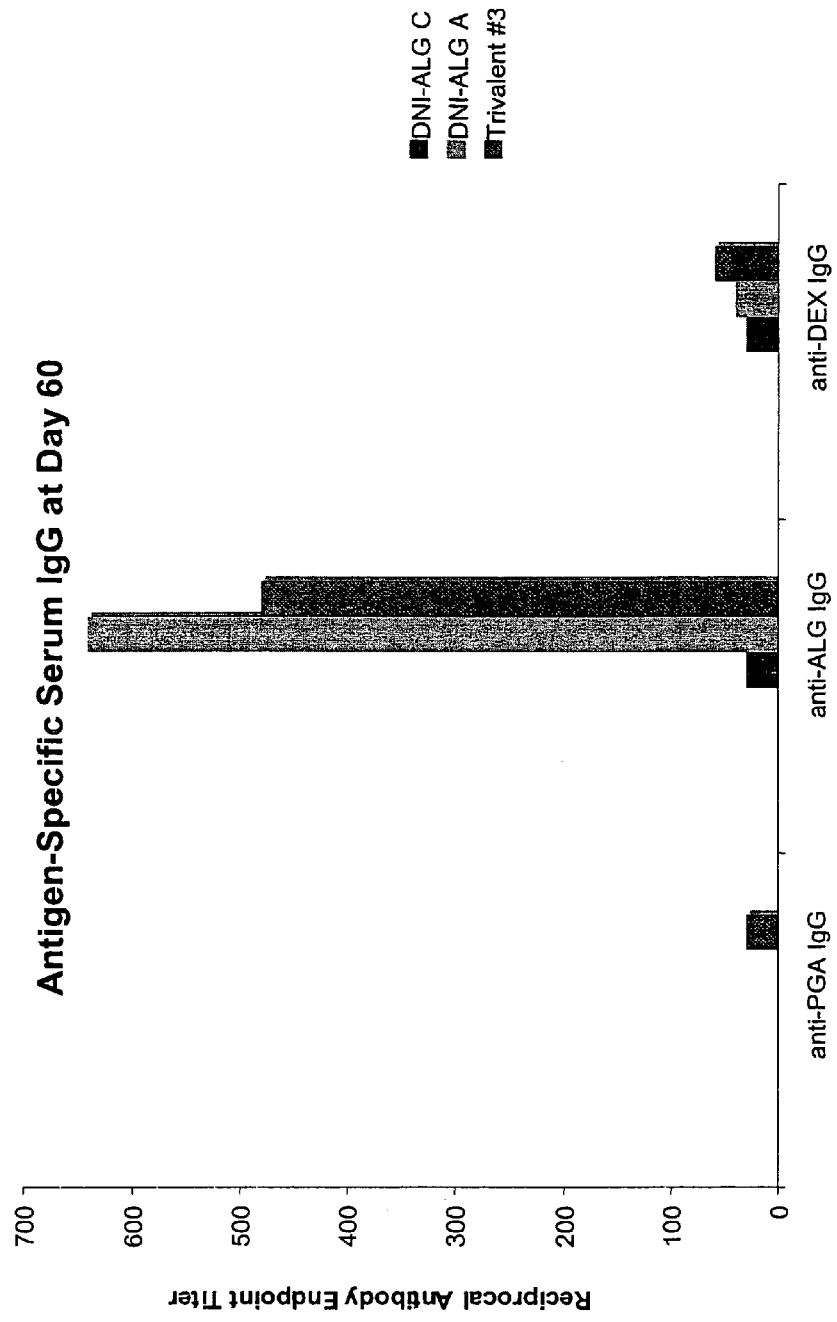
FIG. 7 is a graph showing the antigen-specific serum IgG antibody titer at 60 days after immunization with PCMVs containing DNI and alginate (DNI-ALG C, DNI ALG A) and a "one pot" trivalent PCMV preparation containing DNI complexed with algenate (ALG), dextran (DEX), and PGA.
Figure 8:
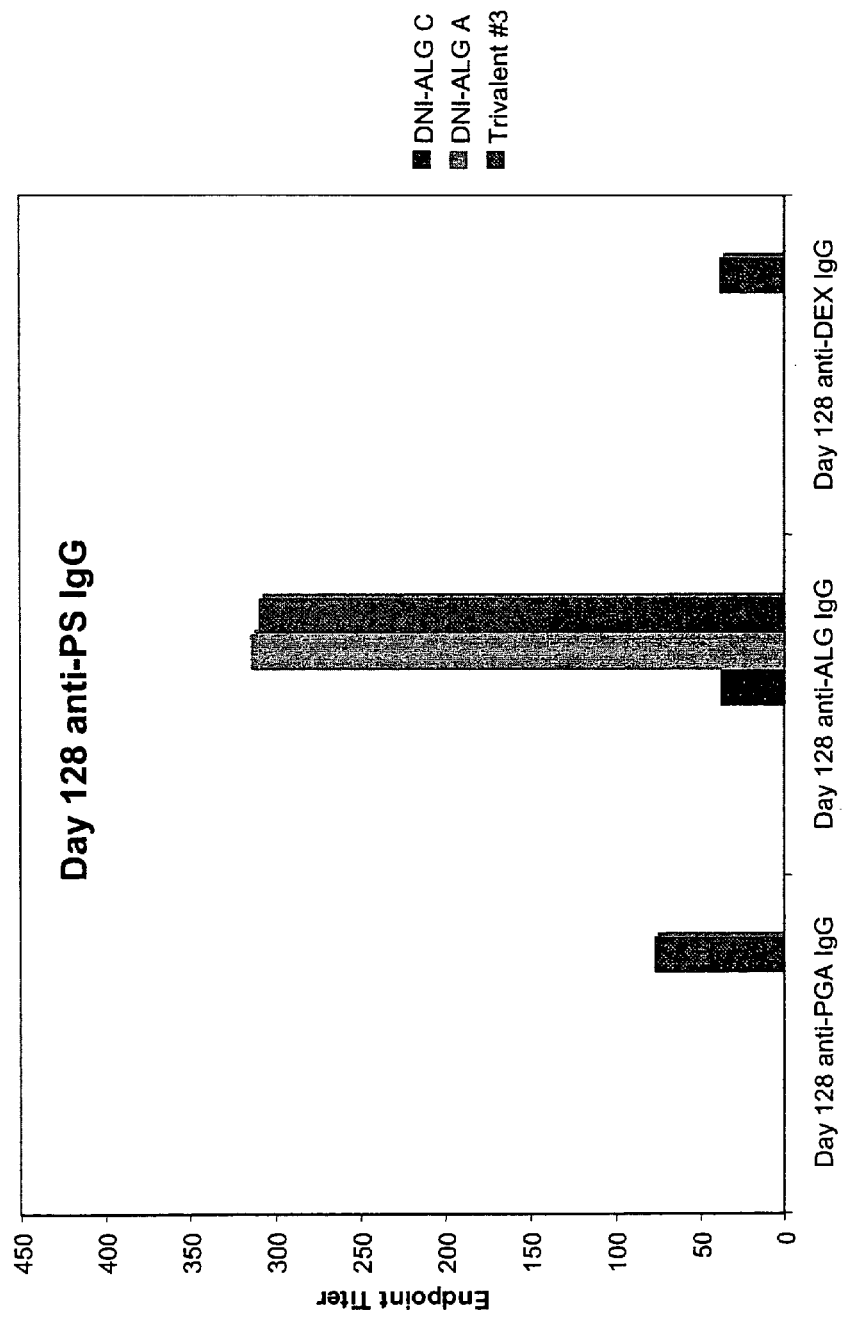
FIG. 8 is a graph showing the anti-PS IgG antibody titer at 128 days after immunization with PCMVs containing DNI and alginate (DNI-ALG C, DNI ALG A) and a "one pot" trivalent PCMV preparation containing DNI complexed with algenate (ALG), dextran (DEX), and PGA.
Figure 9A:
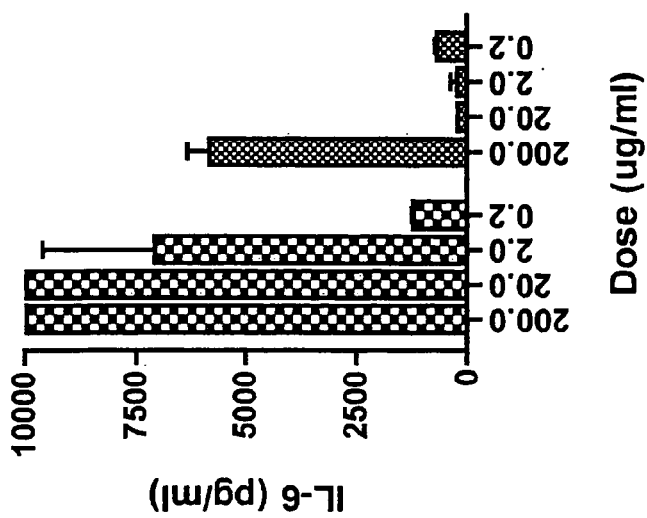
FIGS. 9A and 9B are graphs of IL-6 assays using *S. pneumoniae* polysaccharides (pss) obtained from the American Type Culture Collection and manufactured by Merck or from Serum Institute of India (SII).
Figure 9B:
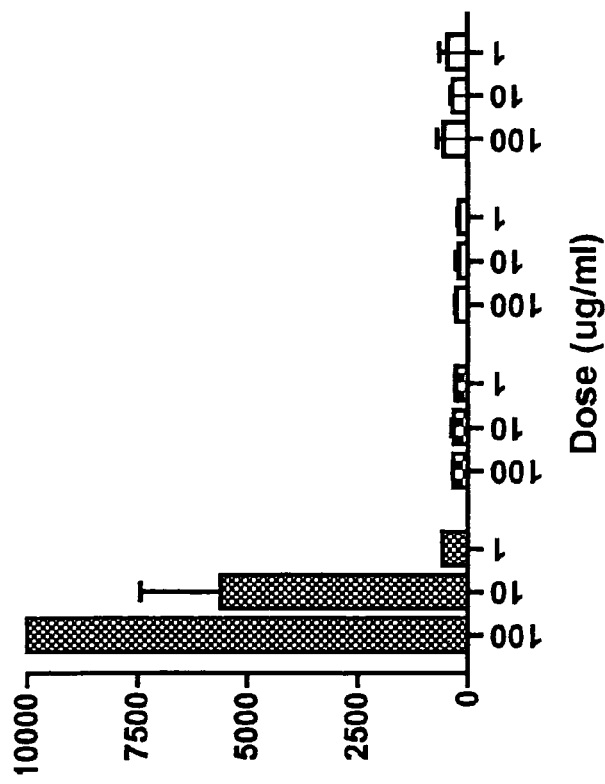
Figure 10:
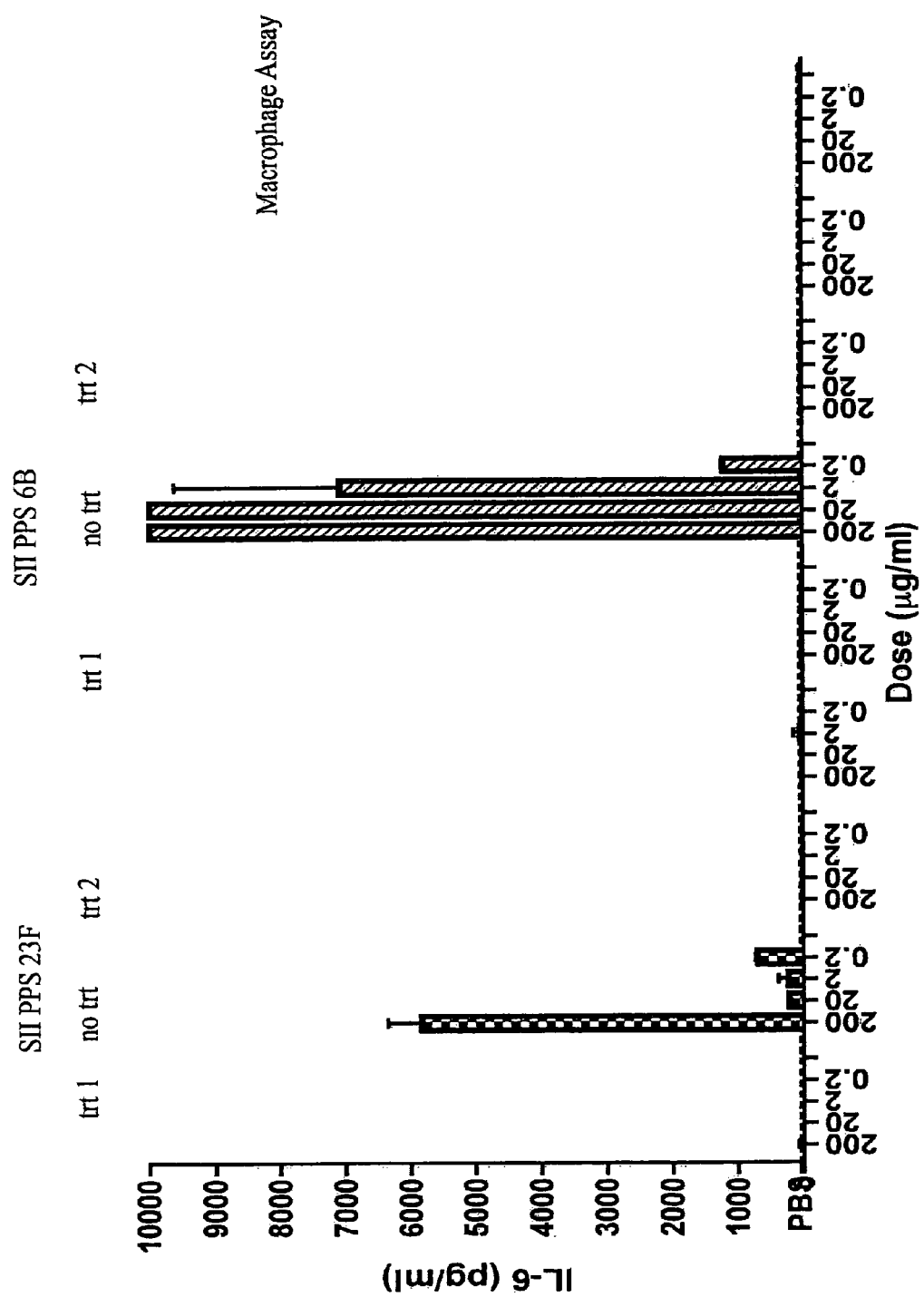
FIG. 10 is a graph showing that the contaminant in pss 6B obtained from SII can be removed using treatment 2 (trt 2; one hour incubation at 80° C. in 1 M NaOH). Treatment 1 (trt 1) is a series of five phenol extractions to remove protein from the polysaccharide.
Figure 11:
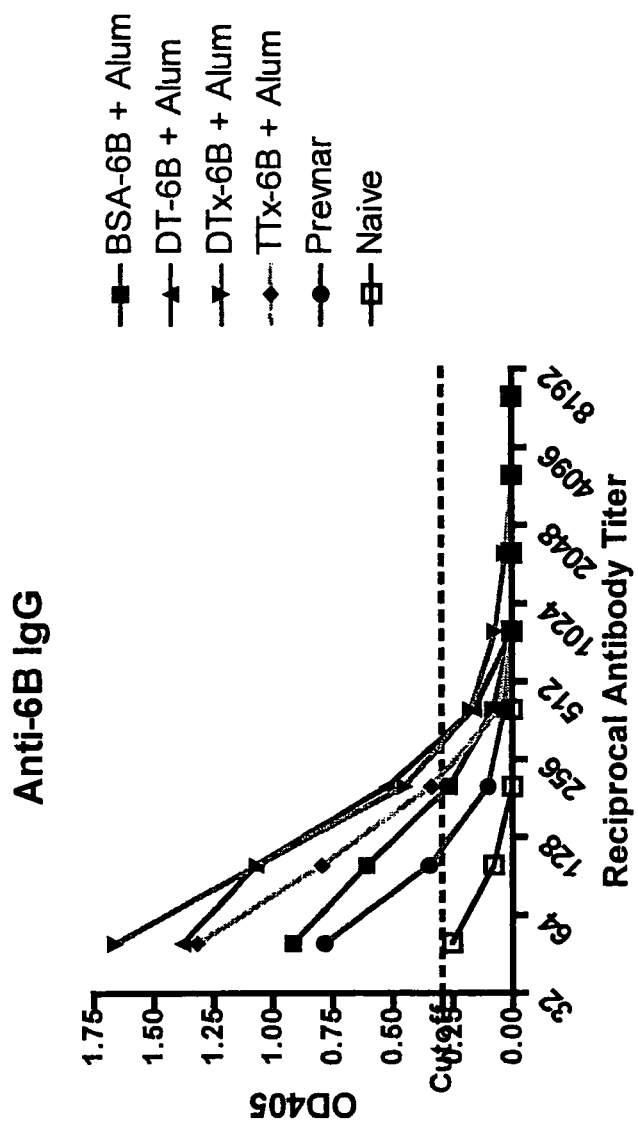
FIG. 11 is a graph showing that PCMVs containing pss 6B are more effective at inducing IgG production than Prevnar®. BSA=Bovine Serum Albumin; DT=Diphtheria toxin; DTx=Diphtheria toxoid; and TTx=Tetanus toxoid.
Figure 12:
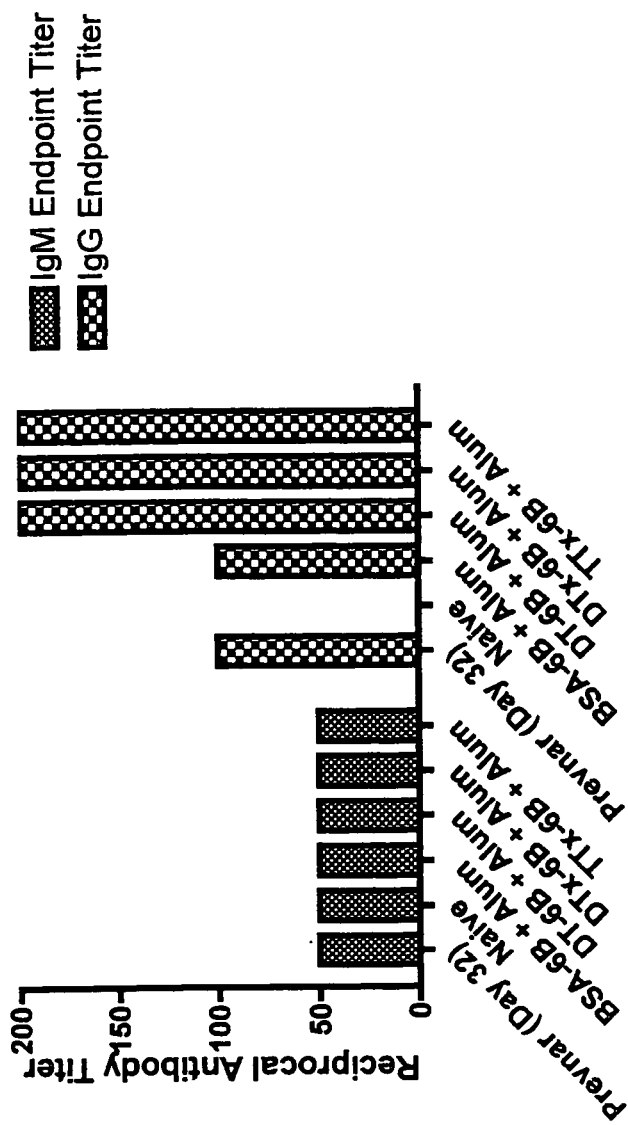
Figure 13:
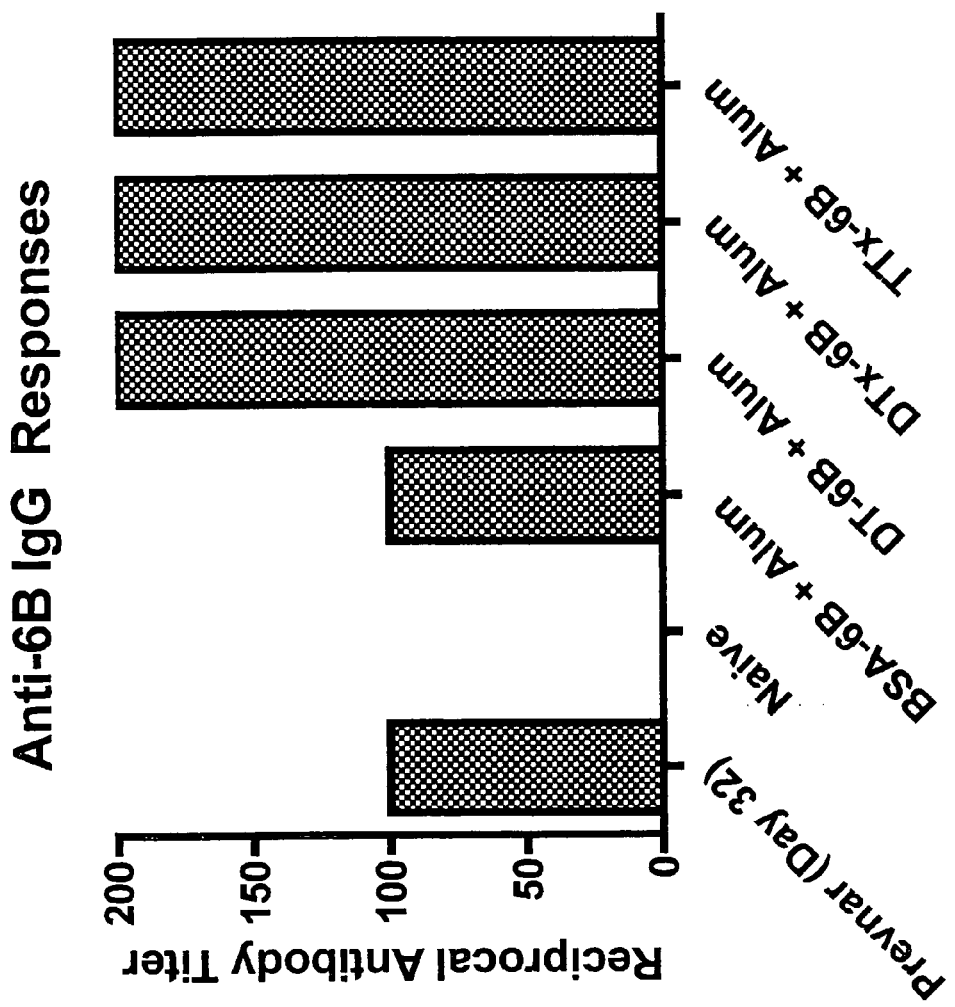
Figure 14:
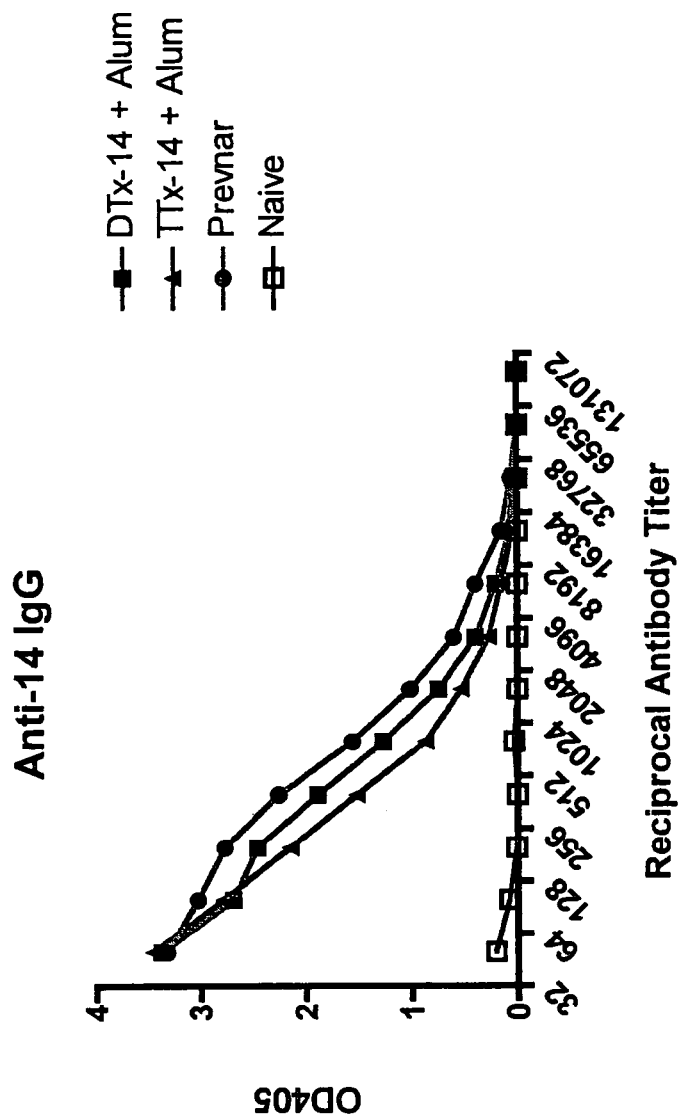
Figure 15:
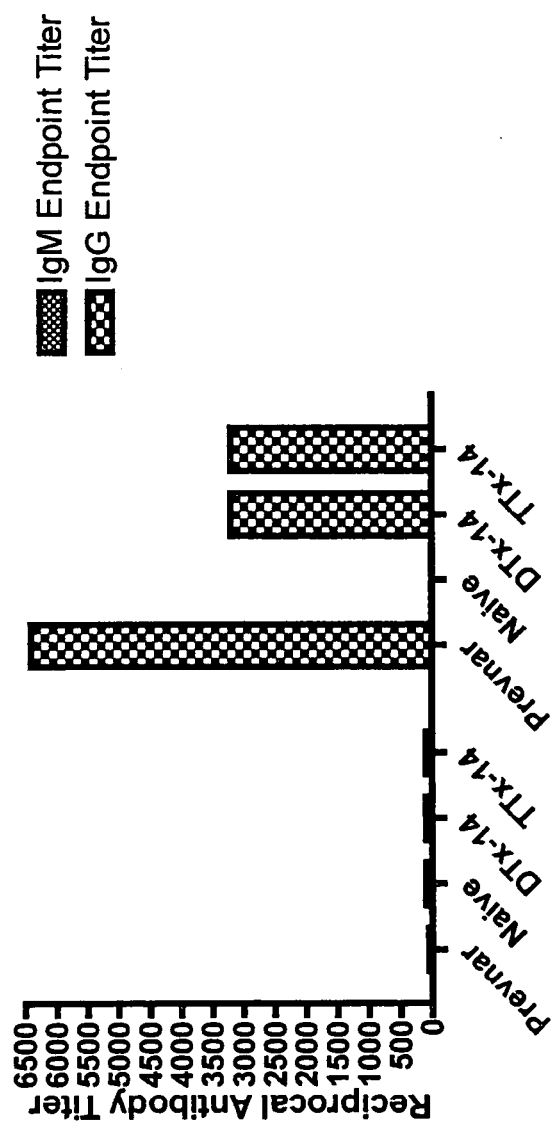
Figure 16:
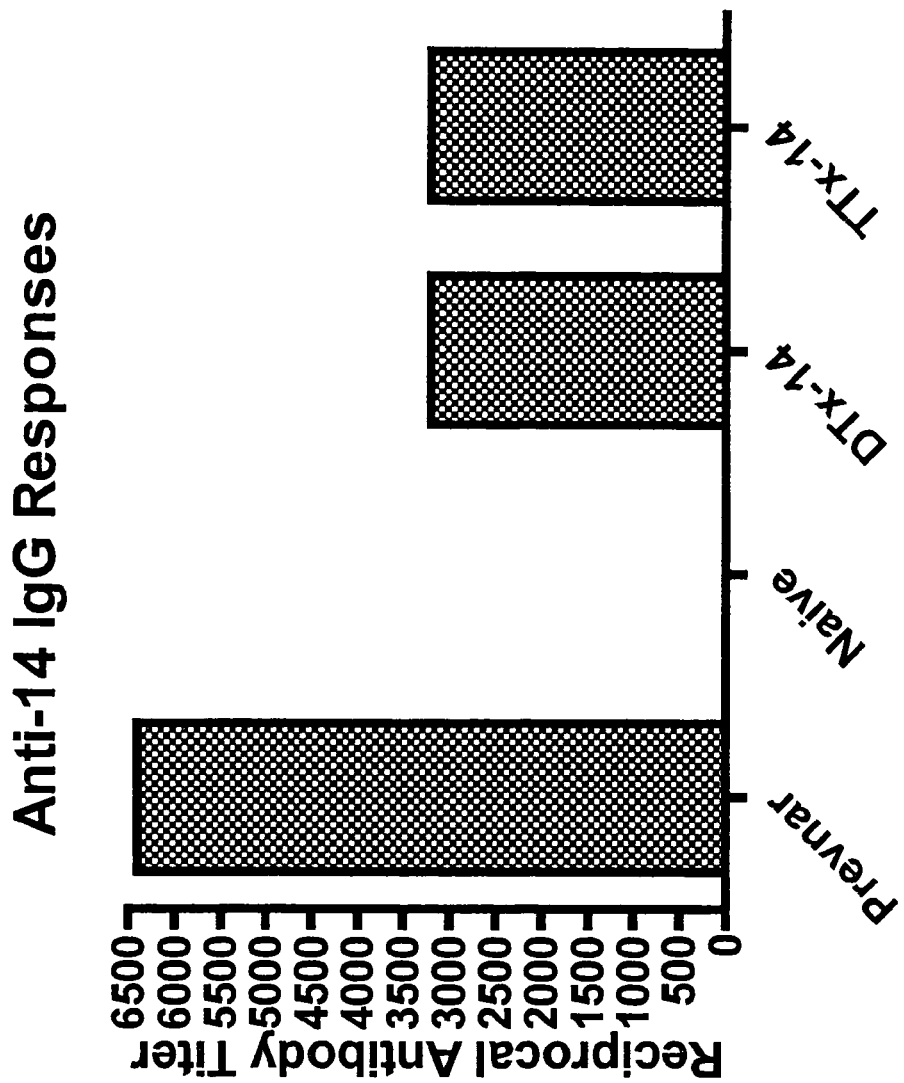

ELISA assays were used to measure the IgM and IgG specific anti-DNI and anti-PGA immune responses in mice immunized with the three PCMV preparations 1-3 and the two antigen control preparations 4 and 5 (FIGS. 3-5). As shown in FIG. 3, the DNI protein was highly immunogenic in all preparations except control preparation 4 which was not cross-linked with glutaraldehyde (no glut). However, these DNI-specific immune responses were exclusively IgG-based. While no anti-DNI IgM was detected even at day 7 of the immunization, a significant anti-DNI IgG response could be detected in mice immunized with PCMV preparations by day 17 and those immunized with cross-linked DNI only (preparation 5). A strong booster response was noted against DNI on day 30 with all preparations including preparation 4.

Anti-PGA IgM responses showed a pattern that was typical of a capsular polymer (FIG. 4). The control preparation 4 generated a detectable anti-PGA IgM response on day 7, but this response was not boosted on day 17 or day 30. All PCMV preparations induced an anti-PGA IgM response on day 7 and then exclusively generated even stronger anti-PGA IgM responses on days 17 and 30. As expected the control preparation 5 (cross-linked DNI only) did not generate either an IgM- or IgG-based anti-PGA response. In marked contrast, PCMV1-3 (preparations 1-3) generated strong IgG-based anti-PGA responses that were apparent on day 17 and then clearly boosted on day 30 (FIG. 5). The IgG-based anti-PGA responses seen for PCMV1-3 were clearly similar to the reported responses to PGA observed for a conventional PGA-DNI conjugate vaccine as reported by Aulinger et al. (Infect. Immun. 73:3408-3414, 2005) and to a PA-PGA conjugate vaccine described by Rhie et al. (Proc. Natl. Acad. Sci. USA 100:10925-10930, 2003). Thus PCMV vaccines #1, #2 and #3 all performed as well as conventional conjugate PGA vaccines by inducing IgG responses to capsular PGA, a known T-independent, protective antigen of *B. anthracis* (Wang et al., Infect. Immun. 72:5460-5463, 2004). The control preparation 5 which contained DNI (not cross-linked) mixed with PGA induced no detectable IgG against PGA indicating DNI does not act as a TLR ligand in stimulating IgG anti-PGA responses in PCMV preparations 1-3. This result also confirms observations in the literature that PGA is a T-cell independent immunogen of low immunogenicity unless it is coupled to protein through covalent bonds (Rhie et al., Proc. Natl. Acad. Sci. USA 100:10925-10930, 2003). The PCMV method apparently converts PGA to a T-cell dependent immunogen despite the fact that the method does not result in cross-linking of the DNI protein directly to PGA molecules.

These data support that the PCMV method can produce immunogens with properties similar to conventional conjugate vaccine. The PGA PCMV was readily made using the methods described herein and was found to induce immune responses typical of PGA-protein conjugate vaccines. The small-scale reactions detailed in Table 1 produced enough PCMV to immunize 1000 mice based on the dosage scheme outlined in FIG. 3. The present data support that PCMV made from PGA and DNI can be used as a vaccine to protect against anthrax caused by *Bacillus anthracis*.

Example 3

Generation and Characterization of Additional PCMVs

The PCMV technology can be applied to capsular antigens of various structures and ionic charges. 23 types of *Streptococcus pneumonia* PS's were purchased from the American Type Culture Collection (ATCC) and are manufactured by Merck, Inc. These PS vary widely in their molecular structure and include PS's that are strongly anionic, partially cationic, neutral in charge, phosphorylated, linear, have branching structures, and modified in various other ways. In preliminary experiments, a subset of these PS that correspond to the seven capsular types in the Wyeth product Prevnar (4, 6B, 9V, 14, 18C, 19F, and 23F) were assayed for their ability to induce IL-6 production by mouse macrophages. Type 4 PS was active in this assay; lipopolysaccharide (LPS) was the control for a TLR agonist. Other PSs (e.g., type 3), PGA, and O antigen PS from *F. tularensis* as well as a PCMV vaccine made from PGA-DNI and a non-cross-linked control were also assayed. This experiment showed that Type 3 pneumococcus PS, and to a lesser extent PGA, was also contaminated with a TLR agonist. The PS from *F. tularensis* and the PCMV were comparably clean in the assay. Phenol extraction and ethanol precipitation could "clean up" (remove residual unknown TLR agonists) *S. pneumoniae* PS type 3 after two consecutive treatments. Accordingly, six *S. pneumoniae* PSs and the *F. tularensis* O antigen PS were found to be clean for IL6 production and these have been explored in experiments described herein.

PCMVs for the seven PS found to be clean for IL6 production have been synthesized using DNI as the carrier protein by a method analogous to that described in Example 1. Preliminary immunogenicity assays suggest that all seven PCMVs were immunogenic to varying degrees. A DNI-based "monovalent" PCMV for *S. pneumoniae* PS14 (14-PCMV) was found to induce high titers of anti-PPS14 IgG that boosted significantly after the third immunization. Remarkably, the same immune response was seen when 14-PCMV was mixed with the other six PCMVs to make a "cocktail" immunogen. Because Prevnar® is an alum absorbed "adjuvanted" vaccine, whether the hexavalent PCMV cocktail could also be absorbed to the alum adjuvant was determined. The results of an immuno assay that qualitatively measures the amount of *S. pneumoniae* PS absorbed to alum after exposure to PCMV or to a control mixture of the same PSs mixed with DNI protein but not glutaraldehyde cross-linked showed that much more PS absorbed to alum in the context of a PCMV than the control (PS+DNI protein un-cross-linked) (as indicated by the higher level of immunoreactivity for the PCMV which dilutes out further in the immunoassay).

Immunization of mice was used to assess the immunogenicity of the heptavalent PCMV with or without absorption to alum adjuvant. Alum adjuvant improved the kinetics of the immune response to PS14, inducing IgG against this PS 7 days sooner than non-adjuvanted vaccine. However, the heptavalent PCMV was more immunogenic in the absence of alum than the control non-cross-linked PS+DNI combination was in the presence of alum. This result confirms that the PCMV procedure renders PSs more immunogenic to mice and supports that the PCMV procedure can be used to make cocktails of antigens that perform immunologically like cocktails of conjugate vaccines.

In additional experiments phenol extraction and ethanol precipitation is used to remove contaminating TLR agonists from the 23 pneumococcus polysaccharide commercial preparations. Removal of the contaminants is confirmed by testing the treated PSs for induction of IL-6 by peritoneal macrophages by standard methods. PSs that are devoid of IL-6 induction activity are used for production of PCMV. Other polysaccharides that are used in PCMVs include an O antigen PS purified from *F. tularensis* and PGA capsule from *B. anthracis*. A total of 25 capsular types are examined (23 pneumococcal types, and one each of the tularemia and anthrax types). Each of the 25 capsular types is used to make a PCMV using the DNI protein, essentially by the method described in Example 1. A one to one ratio of PS to protein is used (approximately 1:1 by dry weight) for these initial PCMV preparations. Each preparation is characterized by SDS-PAGE for evidence of protein cross-linking which has correlated perfectly with the immunogenicity of various PCMV preparations in preliminary experiments. For some capsular types (e.g., 6B and 23F), other carrier proteins are used to make PCMVs. For these same capsular types (e.g., 6B and 23F), an alternative cross-linking chemistry can be used. All PCMV preparations that show evidence of protein cross-linking (e.g., in SDS-PAGE), are tested for their immunogenicity.

For example, ten different PCMVs using five different matrix proteins and two different antigens are made as follows. The selection of the five matrix proteins is based on their current use in FDA-licensed vaccines or other properties that allow them to serve as tracers for measuring the stability of PCMV preparations. The following matrix proteins are used (1) cholera toxin B subunit (available from SBL Vaccin AB), (2) diphtheria toxin, (3) tetanus toxin Fragment C, "Frag C" (available from Sigma Aldrich), (4) DNI, and (5) beta-galactosidase from *Escherichia coli*

(available from Sigma Aldrich). As capsular antigens poly-D-glutamic acid from *Bacillus anthracis* and *Streptococcus pneumoniae* capsule type 14 (Suarez et al., Appl. Environ. Micobiol. 67:969-971, 2001) are used. Both of these capsular antigens are highly immunogenic when used with DNI as a matrix protein in corresponding PCMVs. Each capsule antigen is combined with each of the five selected matrix proteins to produce 10 distinct PCMVs.

PCMVs can be tested for their ability to induce, in mice, isotype antibody switching to IgG as is observed in conventional conjugate vaccines. All antigens can be absorbed to alum and then typically groups of 5 mice per PCMV preparation are used. Mice are pre-bled to obtain baseline immune responses to the test antigens. Mice are then immunized three times (at day 0, 7, 14) by standard IP injection protocol and blood is collected at days 10, 20, 30, and 60 days post primary immunization. Mouse sera are analyzed by standard ELISA assay for IgG against the PS and carrier proteins used. In these experiments, control groups of mice immunized with only PS are included to assess the ability of various PCMV preparations to induce anti-PS IgG compared with the nonconjugated PS which should be poorly- or non-immmunogenic. Promising PCMVs (i.e., PCMVs that induce high levels of IgG against PSs) undergo more careful immunological analysis which seeks to establish the kinetics and dose response aspects of the immune response to the PCMV in mice.

Alternatively, promising PCMVs and their corresponding controls can be sent to commercial vendors for production of rabbit anti-sera. Similar immuno assays are performed to assess the immunogenicity, class of antibody induced, and kinetics of immune response in rabbits. In these experiments the control is the commercial product Prevnar® which is an alum absorbed mixture of 7 different conventional conjugate PS vaccines coupled to CRM197, the nontoxic mutant protein related to diphtheria toxin.

The functionality of the antibody responses induced with PCMVs can be assessed. For example, functionality can be assessed by measuring the ability of the anti-PS antibody to opsonize encapsulated *S. pneumococcus* and lead to bacterial killing after phagocytosis by macrophages. Protection of animals from lethal challenge with *S. pneumococcus* is another way to demonstrate the efficacy of the vaccine in PCMV immunized animals.

Example 4

Comparison to PCMVs to Prevnar®

The relative cleanliness of *S. pneumoniae* polysaccharides (pps) 6B, 14, and 23F obtained from ATCC via Merck or directly from Serum Institute of India (SII) was determined. IL-6 expression was used as an indicator of the cleanliness of a pps and LPS was used as a positive "dirty" control. As shown in FIG. 9A, Merck pps 6B, 14, and 23F are clean, while, as shown in FIG. 9B, pps 6B from SII is "dirty." As shown in FIG. 10, treatment 2 (one hour incubation at 80° C. in 1M NaOH) cleans up SII pps 6B. Clean pps 6B is used for the comparison of conjugate and PCMV immunological properties. As shown in Table 3, the contaminant is not LPS.

TABLE 3

Assay for Endotoxin Levels of Polysaccharides

| Polysaccharides | Endotoxin Units/mg Polysaccharide |
|---|---|
| SII pps 6B - no treatment | 0.75 |
| SII pps 23F - no treatment | 0.85 |
| SII pps 23F - treatment 2 | 0.24 |
| Merck pps various - no treatment | 0.1-0.4 |

FIGS. 11 and 13 show that Prevnar® (which is alum adjuvated) induces IgG antibodies against pps 6B and that the IgG response from alum adjuvated PCMVs (BSA and pps 6B; Diphteria toxin and pps 6B; Diphteria toxoid and pps 6B; and Tetanus toxoid and pps 6B) is better than that observed with Prevnar®. Similarly, as shown in FIG. 12, the IgM response to alum adjuvated PCMVs is similar to that see for Prevnar®.

In addition, for pps 14 (the most immunogenic pps in Prevnar®), as shown in FIGS. 14-16, alum adjuvated PCMVs containing Diphteria toxoid and pps 14 or Tetanus toxoid and pps 14, are approximately equivalent to Prevnar® in inducing an IgG response.

Example 5

Multivalent PCMVs

Multivalent immunogens were produced using the PCMV method by mixing chemically different capsular organic polymers together before cross-linking the DNI carrier protein with glutaraldehyde ("one pot synthetic reaction"). Trivalent immunogens of this sort were made from three organic polymers—PGA, alginate and dextran—using DNI as the carrier. These trivalent vaccines were immunogenic and generated immune responses against the three capsular organic polymers as shown by pooled serum IgM analyzed pre-immunization and after 30 days (FIG. 6), the antigen-specific serum IgG antibody titer 60 days post immunization (FIG. 7), and the anti-PS serum antibody titer 128 days post immunization (FIG. 8). As also shown in FIGS. 6-8, the monovalent alginate PCMV preparations also generated an immune response in mice. Multivalent PCMV immunogens can also be formulated by mixing specific PCMVs that are synthesized separately and then mixed together at the end to produce a "cocktail" vaccine.

All patents, patent applications, patent application publications, and other publications cited or referred to in this specification are herein incorporated by reference to the same extent as if each independent patent, patent application, patent application publication or publication was specifically and individually indicated to be incorporated by reference.

What is claimed is:

1. A method of eliciting an immune response in a subject against an infectious agent, said method comprising administering to a subject in an amount sufficient to induce the production of antibodies in said subject a vaccine composition comprising an antigen of interest and a carrier protein matrix, wherein (i) said carrier protein matrix comprises covalently cross-linked carrier protein molecules, (ii) no more than 50% of said antigen of interest is covalently cross-linked to said carrier protein molecules, and (iii) said antigen is entrapped with said carrier protein matrix to form a complex.

2. The method of claim 1, wherein said method comprises a second administering step wherein said vaccine composition is administered to said subject in an amount sufficient to boost the production of antibodies in said subject.

3. The method of claim 2, wherein said production of antibodies is T-cell dependent.

4. The method of claim 1, wherein said production of antibodies is sufficient to prevent or reduce infection of said subject by an infectious agent.

5. The method of claim 1, wherein said infectious agent is pneumococcus, meningococcus, *Haemophilus influenzae* type B, *Pseudomonas aeruginosa, Francisella tularensis, Shigella* species, *Salmonella* species, *Acinetobacter* species, *Burkholderia* species, and *Escherichia coli*.

6. The method of claim 1, wherein said method comprises a second administering step wherein a second vaccine composition comprising an antigen of interest is provided to said subject in an amount sufficient to boost the production of antibodies in said subject.

7. The method of claim 6, wherein said production of antibodies is sufficient to prevent or reduce infection of said subject by a second infectious agent.

8. The method of claim 1, wherein said antibodies are IgG antibodies.

9. The method of claim 6, wherein said antibodies are IgG antibodies.

10. The method of claim 1, wherein said subject is a human.

11. The method of claim 1, wherein said antigen of interest is a polysaccharide, a polyalcohol, or a poly amino acid.

12. The method of claim 1, wherein said antigen of interest comprises two or more antigens of interest.

13. The method of claim 11, wherein said polysaccharide comprises at least 18 residues.

14. The method of claim 13, wherein said polysaccharide is a *Streptococcus pneumoniae* polysaccharide, *Francisella tularensis* polysaccharide, *Bacillus anthracis* polysaccharide, *Haemophilus influenzae* polysaccharide, *Salmonella typhi* polysaccharide, *Salmonella* species polysaccharide, *Shigella* polysaccharide, or *Neisseria meningitidis* polysaccharide.

15. The method of claim 14, wherein said *Streptococcus pneumoniae* polysaccharide is capsular type 1, 2, 3, 4, 5, 6A, 6B, 7A, 7B, 7C, 7F, 8, 9A, 9L, 9N, 9V, 10A, 10B, 10F, 11A, 11B, 11C, 11D, 11F, 12A, 12B, 12F, 13, 14, 15A, 15B, 15C, 15F, 16A, 16F, 17A, 17F, 18A, 18B, 18C, 18F, 19A, 19B, 19C, 19F, 20, 21, 22F, 23B, 23F, 24A, 24B, 24F, 25A, 25F, 27, 28A, 28F, 29, 31, 32A, 32F, 33A, 33B, 33D, 33F, 34, 35A, 35B, 35F, 36, 37, 38, 39, 40, 41A, 41F, 42, 43, 44, 45, 46, 47A, 47F, or 48.

* * * * *